United States Patent
Hirai et al.

(10) Patent No.: US 9,954,172 B2
(45) Date of Patent: Apr. 24, 2018

(54) ORGANIC SEMICONDUCTOR ELEMENT, MANUFACTURING METHOD THEREOF, ORGANIC SEMICONDUCTOR COMPOSITION, ORGANIC SEMICONDUCTOR FILM, COMPOUND, AND OLIGOMER OR POLYMER

(71) Applicant: FUJIFILM CORPORATION, Minato-ku, Tokyo (JP)

(72) Inventors: Yuki Hirai, Kanagawa (JP); Kensuke Masui, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/593,337

(22) Filed: May 12, 2017

(65) Prior Publication Data
US 2017/0250345 A1 Aug. 31, 2017

Related U.S. Application Data

(63) Continuation of application No. PCT/JP2015/082667, filed on Nov. 20, 2015.

(30) Foreign Application Priority Data

Nov. 25, 2014 (JP) ................. 2014-237886

(51) Int. Cl.
H01L 51/00 (2006.01)
C07D 495/22 (2006.01)
C08G 61/12 (2006.01)
H01L 51/05 (2006.01)

(52) U.S. Cl.
CPC ........ *H01L 51/0036* (2013.01); *C07D 495/22* (2013.01); *C08G 61/124* (2013.01); *C08G 61/126* (2013.01); *H01L 51/0074* (2013.01); *C08G 2261/12* (2013.01); *C08G 2261/1412* (2013.01); *C08G 2261/18* (2013.01); *C08G 2261/3223* (2013.01); *C08G 2261/3241* (2013.01); *C08G 2261/3243* (2013.01); *C08G 2261/411* (2013.01); *C08G 2261/51* (2013.01); *C08G 2261/64* (2013.01); *C08G 2261/92* (2013.01); *H01L 51/0004* (2013.01); *H01L 51/0005* (2013.01); *H01L 51/0545* (2013.01); *H01L 51/0566* (2013.01)

(58) Field of Classification Search
CPC .................................................. H01L 51/0036
See application file for complete search history.

(56) References Cited

U.S. PATENT DOCUMENTS

2011/0288306 A1  11/2011  He et al.

FOREIGN PATENT DOCUMENTS

CN  102659810 A  9/2012
WO  2012060460 A1  5/2012

OTHER PUBLICATIONS

Huiliang Sun et al., "Synthesis and Structure of Bull's Horn-Shaped Oligothienoacene with Seven Fused Thiophene Rings", The Journal of Organic Chemistry, vol. 78, No. 12, Jun. 21, 2013 (Jun. 21, 2013), pp. 6271-6275, XP055379901.
Jianyao Huang et al., "Dibenzoannelated Tetrathienoacene: Synthesis, Characterization, and Applications in Organic Field-Effect Transistors", Organic Letters, 14(23), 6012-6015 CODEN: ORLEF7 ; ISSN: 1523-7052, vol. 14, No. 13, Jul. 6, 2012 (Jul. 6, 2012), pp. 3300-3303, XP055379900.
Extended European Search Report dated Jun. 30, 2017, issued in corresponding EP Patent Application No. 15862559.0.

*Primary Examiner* — Noble E Jarrell
*Assistant Examiner* — John S Kenyon
(74) *Attorney, Agent, or Firm* — SOLARIS Intellectual Property Group, PLLC

(57) ABSTRACT

An object is to provide an organic semiconductor element having excellent carrier mobility and heat resistance of a semiconductor active layer, an organic semiconductor composition for obtaining this element, an organic semiconductor film, and a method of manufacturing an organic semiconductor element in which the composition is used, and another object is to provide a compound and an oligomer or a polymer that are suitably used in the organic semiconductor element, the organic semiconductor composition, the organic semiconductor film, and the method of manufacturing an organic semiconductor element.

The organic semiconductor element of the present invention includes a compound represented by Formula 1 below in a semiconductor active layer. In Formula 1, X represents a chalcogen atom, p and q each independently represent an integer of 0 to 2, and $R^1$ and $R^2$ each independently represent a halogen atom or a group represented by Formula W below.

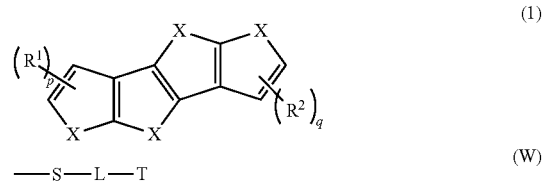

20 Claims, 1 Drawing Sheet

ORGANIC SEMICONDUCTOR ELEMENT, MANUFACTURING METHOD THEREOF, ORGANIC SEMICONDUCTOR COMPOSITION, ORGANIC SEMICONDUCTOR FILM, COMPOUND, AND OLIGOMER OR POLYMER

CROSS-REFERENCE TO RELATED APPLICATION

This application is a continuation application of International Application No. PCT/JP2015/082667, filed Nov. 20, 2015, the disclosure of which is incorporated herein by reference in its entirety. Further, this application claims priority from Japanese Patent Application No. 2014-237886, filed Nov. 25, 2014, the disclosure of which is incorporated herein by reference in its entirety.

BACKGROUND OF THE INVENTION

1. Field of the Invention

The present invention relates to an organic semiconductor element, a manufacturing method thereof, an organic semiconductor composition, an organic semiconductor film, a compound, and an oligomer or a polymer.

2. Description of the Related Art

An organic transistor having an organic semiconductor film (semiconductor active layer) is used in a field effect transistor (FET) used in a liquid crystal display or an organic electroluminescence (EL) display, a radio frequency identifier (RFID, RF Tag), and the like, because lightening of weight, cost reduction, and flexibilization can be achieved.

As an organic transistor material in the related art, those disclosed in CN102659810A or WO2012/060460A are known.

SUMMARY OF THE INVENTION

An object to be achieved by the present invention is to provide an organic semiconductor element having excellent carrier mobility and excellent heat resistance of a semiconductor active layer.

Another object to be achieved by the present invention is to provide an organic semiconductor composition that can form an organic semiconductor having excellent carrier mobility and excellent heat resistance and excellent solution process suitability, an organic semiconductor film, and a method of manufacturing an organic semiconductor element in which the composition is used.

Still another object to be achieved by the present invention is to provide a compound and an oligomer or a polymer that are suitably used in the organic semiconductor element, the organic semiconductor composition, the organic semiconductor film, and the method of manufacturing an organic semiconductor element.

The object of the present invention is solved by the means described in <1>, <16>, <18> to <20>, <31>, and <33> to <36> below. <2> to <15>, <17>, <21> to <30>, and <32> which are preferable embodiments are also described below.

<1> An organic semiconductor element comprising: a compound represented by Formula 1 below in a semiconductor active layer,

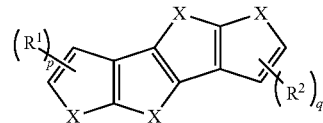

(1)

in Formula 1, X's each independently represent a chalcogen atom, p and q each independently represent an integer of 0 to 2, and $R^1$ and $R^2$ each independently represent a halogen atom or a group represented by Formula W below,

—S-L-T    (W)

in Formula W, S represents a single bond or —(C($R^S$)$_2$)$_n$—, $R^S$'s each independently represent a hydrogen atom or a halogen atom, n represents an integer of 1 to 17, L represents a single bond, a divalent linking group represented by any one of Formulae L-1 to L-15 below, or a divalent linking group obtained by bonding two or more divalent linking groups represented by any one of Formulae L-1 to L-15 below, and T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is two or greater, a siloxane group, an oligosiloxane group having two or more silicon atoms, or a trialkylsilyl group, and

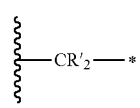

(L-1)

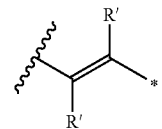

(L-2)

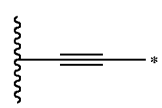

(L-3)

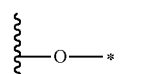

(L-4)

(L-5)

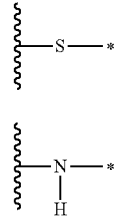

(L-6)

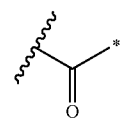

(L-7)

-continued

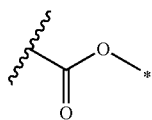
(L-8)

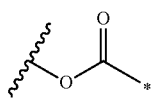
(L-9)

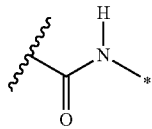
(L-10)

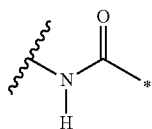
(L-11)

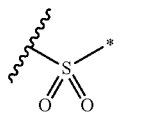
(L-12)

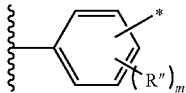
(L-13)

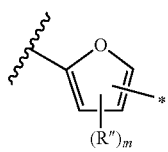
(L-14)

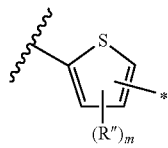
(L-15)

in Formulae L-1 to L-15, a wavy line portion represents a bonding position to S or another divalent linking group represented by any one of Formulae L-1 to L-15, * represents a bonding position to T or another divalent linking group represented by any one of Formulae L-1 to L-15, m in Formula L-13 represents an integer of 0 to 4, m in Formulae L-14 and L-15 represents an integer of 0 to 2, R"s in Formulae L-1 and L-2 each independently represent a hydrogen atom or a substituent, and R'''s in Formulae L-13, L-14, and L-15 each independently represent a substituent.

<2> The organic semiconductor element according to <1>, in which p and/or q in Formula 1 represents 1 or 2.

<3> The organic semiconductor element according to <1> or <2>, in which p and/or q in Formula 1 represents 1 or 2, and $R^1$ and/or $R^2$ represents a group represented by Formula W.

<4> The organic semiconductor element according to any one of <1> to <3>, in which p and q in Formula 1 represent 1.

<5> The organic semiconductor element according to any one of <1> to <4>, in which the compound represented by Formula 1 is a compound represented by Formula 2-1 or 2-2 below,

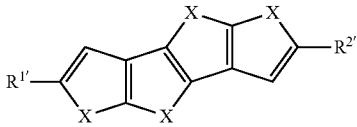
(2-1)

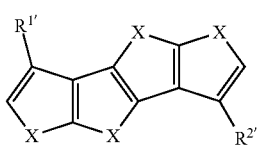
(2-2)

X's in Formula 2-1 and 2-2 each independently represent a chalcogen atom, and $R^{1''}$ and $R^{2'}$ each independently represent a group represented by Formula W.

<6> The organic semiconductor element according to any one of <1> to <5>, in which all X's are S atoms.

<7> The organic semiconductor element according to any one of <1> to <6>, in which a compound represented by Formula 1 is point symmetric about a point A,

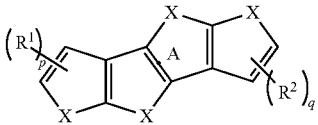
(1)

in this formula, p and q are the same as those in Formula 1 and each represent an integer of 0 to 2, and $R^1$ and $R^2$ are also the same as those in Formula 1 and each represent a halogen atom or a group represented by Formula W.

<8> The organic semiconductor element according to any one of <1> to <7>, in which a sum of the numbers of carbon atoms of a group represented by Formula W is 2 to 40.

<9> The organic semiconductor element according to any one of <1> to <8>, in which L in Formula W represents a divalent linking group represented by any one of Formulae L-1 to L-4 and L-13 to L-15, or a divalent linking group obtained by bonding two or more divalent linking groups represented by any one of Formulae L-1 to L-4 and L-13 to L-15.

<10> The organic semiconductor element according to any one of <1> to <9>, in which L in Formula W represents a divalent linking group represented by any one of Formulae L-1 to L-4 and L-13 to L-15, singly.

<11> The organic semiconductor element according to any one of <1> to <10>, in which S in Formula W is a single bond.

<12> The organic semiconductor element according to any one of <1> to <11>, in which L in Formula W represents a divalent linking group represented by any one of Formulae L-13 to L-15 singly.

<13> The organic semiconductor element according to any one of <1> to <12>, in which T represents an alkyl group.

<14> The organic semiconductor element according to any one of <1> to <13>, in which the group represented by Formula W is an alkyl group.

<15> The organic semiconductor element according to any one of <1> to <14>, which is an organic thin film transistor.

<16> An organic semiconductor composition comprising: a compound represented by Formula 1; and a solvent.

<17> The organic semiconductor composition according to <16>, further comprising: a binder polymer.

<18> A method of manufacturing an organic semiconductor element, comprising: an applying step of applying the organic semiconductor composition according to <16> or <17>to a substrate by an ink jet method or a flexographic printing method; and a removing step of removing at least a portion of the solvent from the applied organic semiconductor composition.

<19> An organic semiconductor film formed from forming the organic semiconductor composition according to <16> or <17>.

<20> An organic semiconductor element, comprising: an oligomer or a polymer having a constitutional repeating unit including a structure represented by Formula 3 below in a semiconductor active layer,

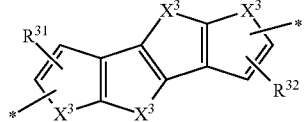

(3)

in Formula 3, $X^3$'s each independently represent a chalcogen atom, $R^{31}$ and $R^{32}$ each independently represent a hydrogen atom, a halogen atom, or a substituent represented by Formula W below, and * represents a bonding position, and

—S-L-T    (W)

in Formula W, S represents a single bond or —(C($R^S$)$_2$)$_n$—, $R^S$'s each independently represent a hydrogen atom or a halogen atom, n represents an integer of 1 to 17, L represents a single bond, a divalent linking group represented by any one of Formulae L-1 to L-15 below, or a divalent linking group obtained by bonding two or more divalent linking groups represented by any one of Formulae L-1 to L-15 below, and T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is 2 or greater, a siloxane group, an oligosiloxane group having two or more silicon atoms, or a trialkylsilyl group, and

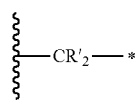

(L-1)

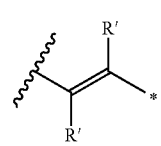

(L-2)

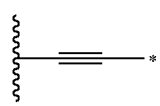

(L-3)

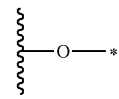

(L-4)

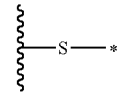

(L-5)

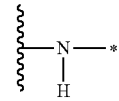

(L-6)

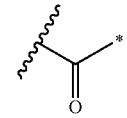

(L-7)

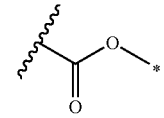

(L-8)

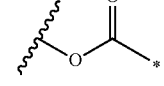

(L-9)

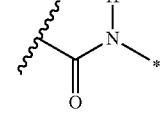

(L-10)

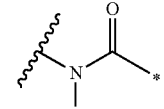

(L-11)

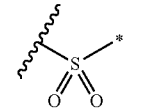

(L-12)

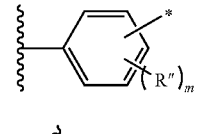

(L-13)

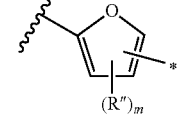

(L-14)

(L-15)

in Formulae L-1 to L-15, a wavy line portion represents a bonding position to S or another divalent linking group represented by any one of Formulae L-1 to L-15, * represents a bonding position to T or another divalent linking group represented by any one of Formulae L-1 to L-15, m in Formula L-13 represents an integer of 0 to 4, m in Formulae L-14 and L-15 represents an integer of 0 to 2, R"s in Formulae L-1 and L-2 each independently represent a hydrogen atom or a substituent, and R'''s in Formulae L-13, L-14, and L-15 each independently represent a substituent.

<21> The organic semiconductor element according to <20>, in which an oligomer or a polymer having a constitutional repeating unit including a structure represented by Formula 3 is conjugated in a main chain direction.

<22> The organic semiconductor element according to <20> or <21>, in which a constitutional repeating unit including a structure represented by Formula 3 further includes a structure represented by Formula Z below,

in Formula Z, $Ar^1$ and $Ar^2$ each independently represent a single bond, a vinylene group, an ethynylene group, an arylene group, a heteroarylene group, or a divalent group obtained by bonding two or more of these, and V represents a single bond or a divalent conjugate group having 2 to 40 carbon atoms, p represents 1 to 6, and two or more V's may be identical to or different from each other when p is 2 or greater, here, all of $Ar^1$, $Ar^2$, and V are not simultaneously single bonds.

<23> The organic semiconductor element according to <22>, in which the oligomer or the polymer having a constitutional repeating unit including a structure represented by Formula 3 is an oligomer or a polymer obtained by linking a structure represented by Formula 3 and a structure represented by Formula Z with each other.

<24> The organic semiconductor element according to <22> or <23>, in which V in Formula Z represents a divalent linking group represented by any one of Formulae $V_D$-1 to $V_D$-16, and $V_A$-1 to $V_A$-11 below, and

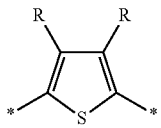
($V_D$-1)

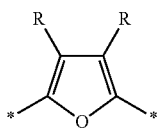
($V_D$-2)

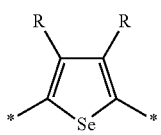
($V_D$-3)

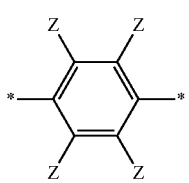
($V_D$-4)

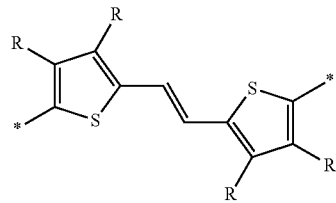
($V_D$-5)

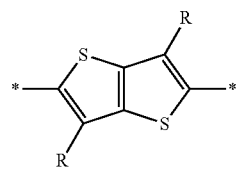
($V_D$-6)

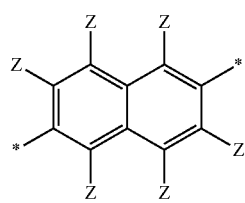
($V_D$-7)

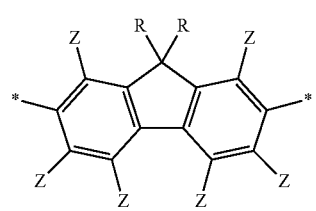
($V_D$-8)

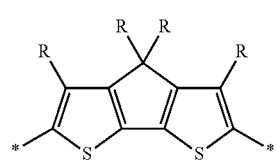
($V_D$-9)

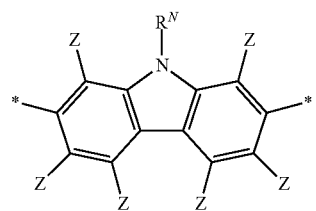
($V_D$-10)

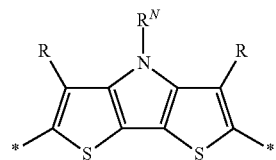
($V_D$-11)

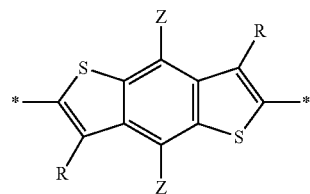
($V_D$-12)

(V_D-13) 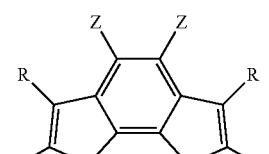
(V_D-14) 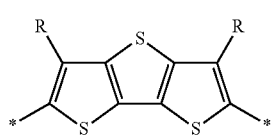
(V_D-15) 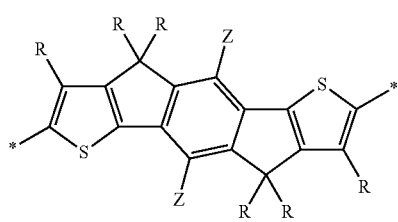
(V_D-16) 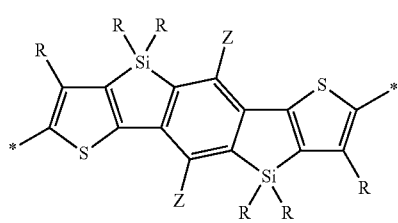
(V_A-1) 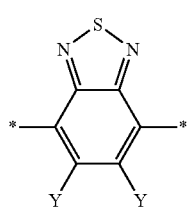
(V_A-2) 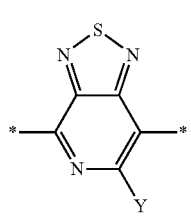
(V_A-3) 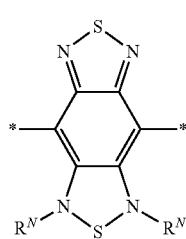
(V_A-4) 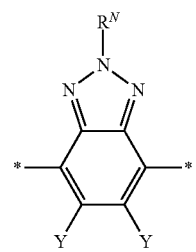
(V_A-5) 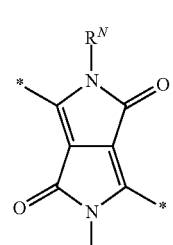
(V_A-6) 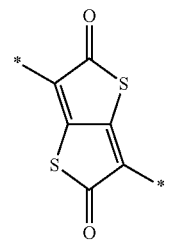
(V_A-7) 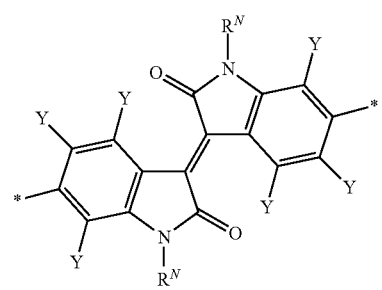
(V_A-8) 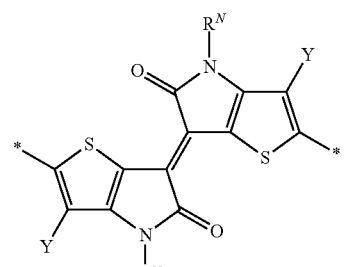
(V_A-9) 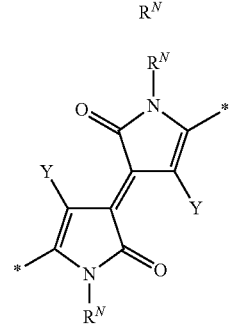

-continued

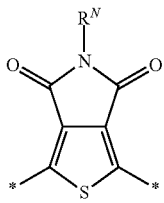
(V$_A$-10)

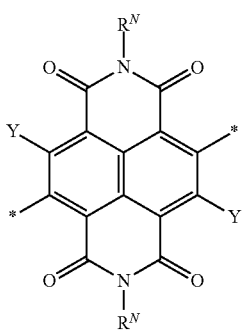
(V$_A$-11)

R's in Formulae V$_D$-1 to V$_D$-3, V$_D$-5, V$_D$-6, V$_D$-8, V$_D$-9, and V$_D$-11 to V$_D$-16 each independently represent a hydrogen atom, a halogen atom, or an alkyl group, R's adjacent to each other may be bonded to each other to form a ring, Z's in Formulae V$_D$-4, V$_D$-7, V$_D$-8, V$_D$-10, V$_D$-12, V$_D$-13, V$_D$-15, and V$_D$-16 each independently represent a hydrogen atom, a halogen atom, an alkyl group, or an alkoxy group, Z's adjacent to each other may be bonded to each other to form a ring, R$^N$'s in Formulae V$_D$-10, V$_D$-11, V$_A$-3, V$_A$-4, V$_A$-5, and V$_A$-7 to V$_A$-11 each independently represent an alkyl group, R$^N$'s adjacent to each other may be bonded to each other to form a ring, and Y's in Formulae V$_A$-1, V$_A$-2, V$_A$-4, V$_A$-7 to V$_A$-9, and V$_A$-11 each independently represent a hydrogen atom, an alkyl group, an alkoxy group, CN, or a halogen atom, Y's adjacent to each other may be bonded to each other to form a ring, and * represents a bonding position.

<25> The organic semiconductor element according to any one of <22> to <24>, in which p in Formula Z represents 1.

<26> The organic semiconductor element according to any one of <22> to <25>, in which Ar$^1$ and Ar$^2$ in Formula Z each independently represent a single bond or a divalent linking group represented by Formula Ar-1 or Ar-2 below,

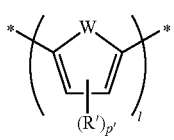
(Ar-1)

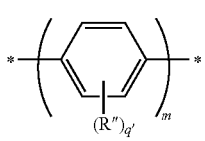
(Ar-2)

in Formula Ar-1, R''s each independently represent an alkyl group, p' represents an integer of 0 to 2, R''s adjacent to each other may form a ring, W represents a chalcogen atom, and l represents an integer of 1 to 4, and R'''s in Formula Ar-2 each independently represent an alkyl group or an alkoxy group, q' represents an integer of 0 to 4, R'''s adjacent to each other may form a ring, and m represents an integer of 1 to 4.

<27> The organic semiconductor element according to any one of <22> to <26>, in which V in Formula Z represents a divalent linking group represented by any one of V$_A$-1 to V$_A$-11.

<28> The organic semiconductor element according to any one of <20> to <27>, in which a number-average molecular weight of the oligomer or polymer having a constitutional repeating unit including a structure represented by Formula 3 is 30,000 or greater.

<29> The organic semiconductor element according to any one of <20> to <28>, in which a number-average molecular weight of the oligomer or polymer having a constitutional repeating unit including a structure represented by Formula 3 is 150,000 or less.

<30> The organic semiconductor element according to any one of <20> to <29>, which is an organic thin film transistor.

<31> An organic semiconductor composition, comprising: an oligomer or a polymer having a repeating unit including a structure represented by Formula 3, and a solvent.

<32> The organic semiconductor composition according to <31>, further comprising: a binder polymer.

<33> A method of manufacturing an organic semiconductor element, comprising: an applying step of applying the organic semiconductor composition according to <31> or <32>to a substrate by an ink jet method or a flexographic printing method, and a removing step of removing at least a portion of the solvent from the applied organic semiconductor composition.

<34> An organic semiconductor film formed from the organic semiconductor composition according to <31> or <32>.

<35> A compound represented by Formula 1.

<36> An oligomer or a polymer, comprising: a constitutional repeating unit including a structure represented by Formula 3.

According to the present invention, it is possible to provide an organic semiconductor element having excellent carrier mobility and excellent heat resistance of a semiconductor active layer.

According to the present invention, it is possible to provide an organic semiconductor composition that can form an organic semiconductor having excellent carrier mobility and excellent heat resistance and excellent solution process suitability, an organic semiconductor film, and a method of manufacturing an organic semiconductor element in which the composition is used.

According to the present invention, it is possible to provide a compound and an oligomer or a polymer that are suitably used in the organic semiconductor element, the organic semiconductor composition, the organic semiconductor film, and the method of manufacturing an organic semiconductor element.

DESCRIPTION OF THE PREFERRED EMBODIMENTS

Figure 1:
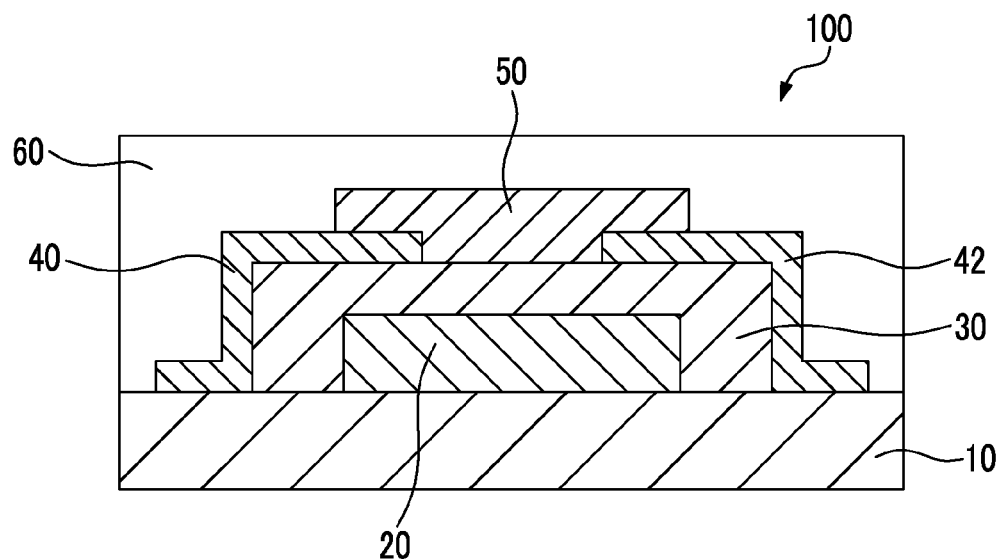
FIG. 1 is a schematic cross-sectional view of an aspect of an organic semiconductor element of the present invention.

Hereinafter, the contents of the present invention will be specifically described. The constituents in the following description will be explained based on typical embodiments of the present invention, but the present invention is not limited to the embodiments. In the specification of the present application, "to" is used to mean that the numerical values listed before and after "to" are a lower limit and an upper limit respectively.

In the present specification, in a case where there is no description regarding whether a group (atomic group) is substituted or unsubstituted, the group includes both of a group having a substituent and a group not having a substituent. For example, an "alkyl group" includes not only an alkyl group not having a substituent (unsubstituted alkyl group) but also an alkyl group having a substituent (substituted alkyl group).

In the present specification, in some cases, a chemical structural formula is described as a simplified structural formula in which a hydrogen atom is omitted.

In the present invention, "mobility" refers to "carrier mobility" and means any one or both of electron mobility and hole mobility.

In the present invention, "mass %" and "weight %" have the same definition, and "part by mass" and "part by weight" have the same definition.

In the present invention, a combination of preferred aspects is more preferable.

(Organic Semiconductor Element)

A first organic semiconductor element according to the present invention includes a compound (hereinafter, also referred to as a specific compound) represented by Formula 1 below in a semiconductor active layer.

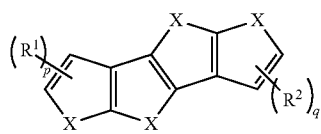
(1)

In Formula 1, X represents a chalcogen atom, p and q each independently represent an integer of 0 to 2, and $R^1$ and $R^2$ each independently represent a halogen atom or a group represented by Formula W below.

—S-L-T    (W)

In Formula W, S represents a single bond or —(C($R^S$)$_2$)$_n$—, $R^S$'s each independently represent a hydrogen atom or a halogen atom, n represents an integer of 1 to 17, L represents a single bond, a divalent linking group represented by any one of Formulae L-1 to L-15 below, or a divalent linking group obtained by bonding two or more divalent linking groups represented by any one of Formulae L-1 to L-15 below, and T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is 2 or greater, a siloxane group, an oligosiloxane group having two or more silicon atoms, or a trialkylsilyl group.

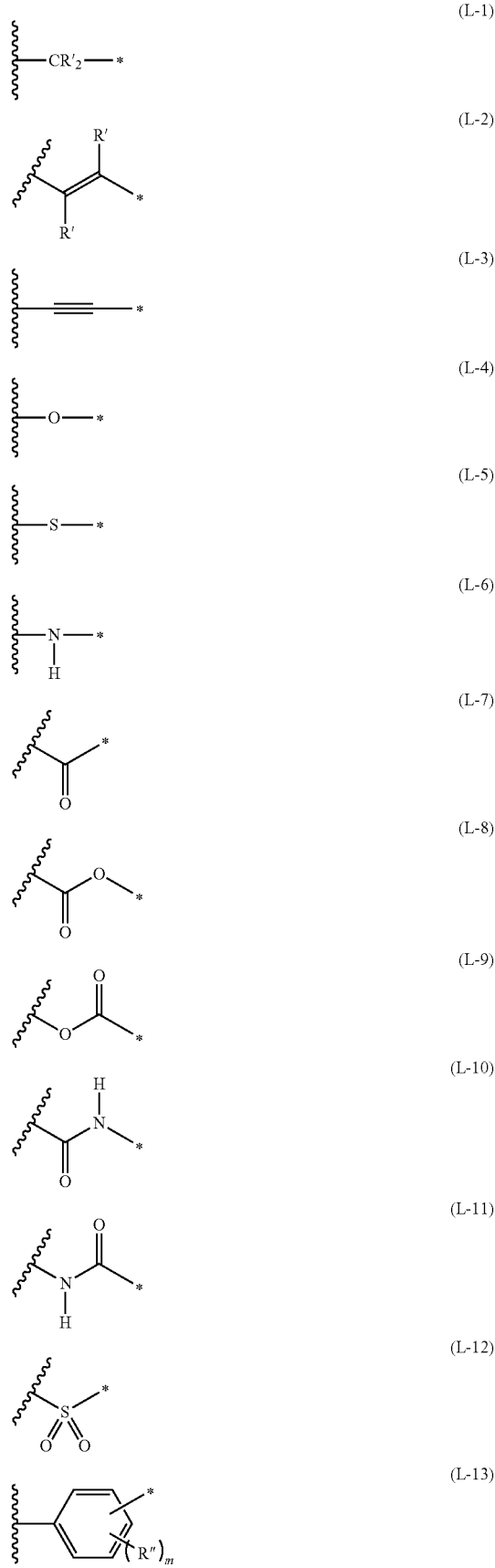

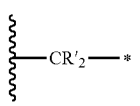 (L-1)

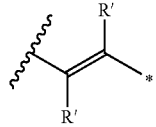 (L-2)

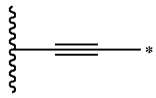 (L-3)

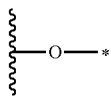 (L-4)

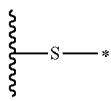 (L-5)

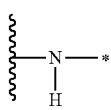 (L-6)

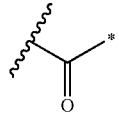 (L-7)

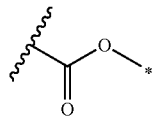 (L-8)

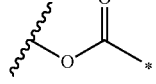 (L-9)

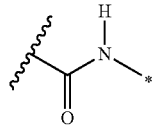 (L-10)

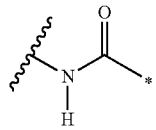 (L-11)

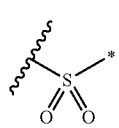 (L-12)

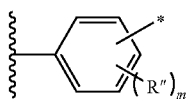 (L-13)

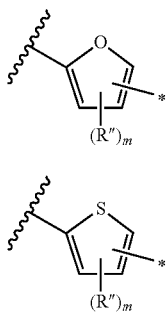 (L-14)

(L-15)

In Formulae L-1 to L-15, a wavy line portion represents a bonding position to S or another divalent linking group represented by any one of Formulae L-1 to L-15, * represents a bonding position to T or another divalent linking group represented by any one of Formulae L-1 to L-15, m in Formula L-13 represents an integer of 0 to 4, m in Formulae L-14 and L-15 represents an integer of 0 to 2, R″s in Formulae L-1 and L-2 each independently represent a hydrogen atom or a substituent, and R‴s in Formulae L-13, L-14, and L-15 each independently represent a substituent. Here, the "substituent" is preferably an inert atom (group) that does not influence on semiconductor characteristics, examples thereof include an alkyl group, and m is preferably 0 in the same manner as below.

A second organic semiconductor element according to the present invention contains an oligomer or a polymer (hereinafter, also referred to as a specific polymer compound) having a constitutional repeating unit including a structure represented by Formula 3 below in a semiconductor active layer.

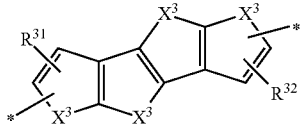 (3)

In Formula 3, $X^3$'s each independently represent a chalcogen atom, $R^{31}$ and $R^{32}$ each independently represent a hydrogen atom, a halogen atom, or a substituent represented by Formula W below, and * represents a bonding position.

—S-L-T  (W)

In Formula W, S represents a single bond or —(C(R$^S$)$_2$)$_n$—, R$^S$'s each independently represent a hydrogen atom or a halogen atom, n represents an integer of 1 to 17, L represents a single bond, a divalent linking group represented by any one of Formulae L-1 to L-15 below, or a divalent linking group obtained by bonding two or more divalent linking group represented by any one of Formulae L-1 to L-15 below, and T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is 2 or greater, a siloxane group, an oligosiloxane group having two or more silicon atoms, or a trialkylsilyl group.

-continued (L-14)

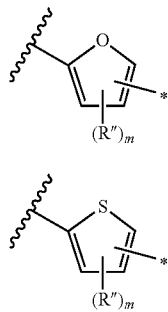

(L-15)

In Formulae L-1 to L-15, a wavy line portion represents a bonding position to S or a divalent linking group represented by any one of another Formulae L-1 to L-15, * represents a bonding position to T or another divalent linking group represented by any one of Formulae L-1 to L-15, m in Formula L-13 represents an integer of 0 to 4, m in Formulae L-14 and L-15 represents an integer of 0 to 2, R″s in Formulae L-1 and L-2 each independently represent a hydrogen atom or a substituent, and R‴s in Formulae L-13, L-14 and L-15 each independently represent a substituent.

As a result of diligent research by the present inventors, the present inventors have found that, if a specific compound or a specific polymer compound was contained in a semiconductor active layer, it was possible to obtain an organic semiconductor element having excellent carrier mobility and excellent heat resistance of a semiconductor active layer, so as to complete the present invention. The present inventors have also found that an organic semiconductor composition including a specific compound or a specific polymer compound had an excellent process.

The mechanism of exhibiting a specific effect is not clear. However, it is assumed that the effect of the present invention was exhibited since a specific compound and a specific polymer compound had a specific fused polycyclic aromatic ring structure.

Hereinafter, an organic semiconductor element according to the present invention is described.

<Compound represented by Formula 1>

The first organic semiconductor element according to the present invention includes a compound (specific compound) represented by Formula 1 above includes a semiconductor active layer.

The compound represented by Formula 1 is an organic semiconductor compound.

X represents a chalcogen atom (an O atom, a S atom, a Se atom, and a Te atom) and preferably a S atom or a Se atom, and more preferably a S atom. In the aforementioned aspect, the carrier mobility of the obtained organic semiconductor film is more excellent.

p and q each independently represent an integer of 0 to 2. If p and q are not 0 at the same time, that is, p+q is preferably 1 or greater. It is more preferable that p and/or q is 1 or 2, it is even more preferable that p and q are 1 or 2, and it is particularly preferable that p and q are 1. In a case where both of p and q are 1, substitution positions of $R^1$ and $R^2$ are preferably the second position from the outermost ring. It is preferable that at least one of 1e and $R^2$ is a group represented by Formula W below, it is more preferable that both of $R^1$ and $R^2$ are groups represented by Formula W below, and it is even more preferable that p and q are 1, and both of $R^1$ and $R^2$ are groups represented by Formula W below.

The specific compound is preferably a compound represented by Formula 2-1 below and a compound represented by Formula 2-2 below and more preferably a compound represented by Formula 2-1.

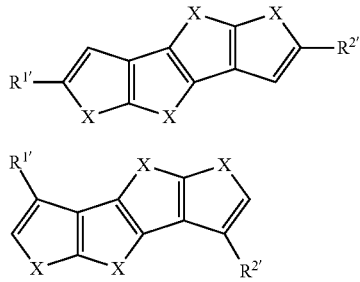

In Formulae 2-1 and 2-2, X's each independently represent a chalcogen atom, $R^{1'}$ and $R^{2'}$ each independently represent a group represented by Formula W below.

In Formulae 2-1 and 2-2, X represents a chalcogen atom (an O atom, a S atom, a Se atom, and a Te atom), preferably a S atom or a Se atom, and more preferably a S atom. In the aforementioned aspect, carrier mobility of the obtained organic semiconductor film is more excellent.

$R^{1'}$ and $R^{2'}$ each independently represent a group represented by Formula W below.

In the aforementioned aspect, heat resistance and mobility of the obtained semiconductor active layer are more excellent, and solution process suitability is excellent.

$R^1$ and $R^2$ each independently represent a halogen atom or a group represented by Formula W below. As described above, a group represented by Formula W below is preferable. In the aforementioned aspect, carrier mobility of the obtained organic semiconductor film is more excellent.

—S-L-T       (W)

S represents a single bond or —(C($R^S$)$_2$)$_n$—, preferably a single bond or an unsubstituted methylene group, and more preferably a single bond.

$R^S$'s each independently represent a hydrogen atom or a halogen atom and is preferably a hydrogen atom.

n represents an integer of 1 to 17, preferably an integer of 1 to 8, and more preferably an integer of 1 to 4.

In view of coating film formability and heat resistance of the obtained organic semiconductor film, $R^1$ and $R^2$ are preferably the same groups.

The number of carbon atoms of $R^1$ is preferably 5 to 40 and more preferably 8 to 20.

The number of carbon atoms of $R^2$ is preferably 5 to 40 and more preferably 8 to 20.

L represents a single bond, a divalent linking group represented by any one of Formulae L-1 to L-15 below, or a divalent linking group obtained by bonding two or more divalent linking groups represented by any one of Formulae L-1 to L-15 below.

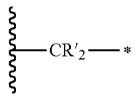

(L-1)

-continued

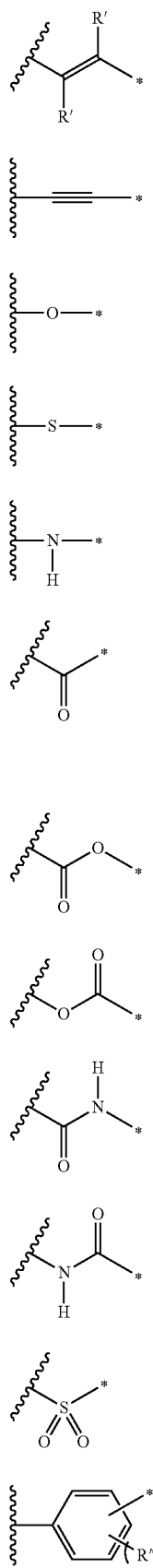

(L-2)
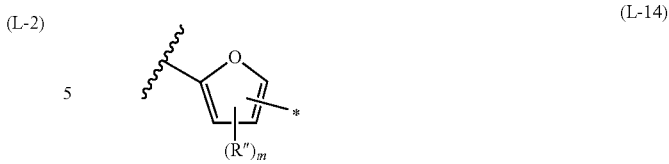

(L-3)

(L-4)

(L-5)

(L-6)

(L-7)

(L-8)

(L-9)

(L-10)

(L-11)

(L-12)

(L-13)

-continued (L-14)

(L-15)
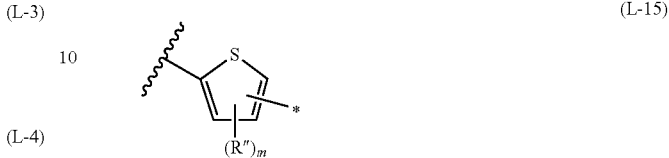

In Formulae L-1 to L-15, a wavy line portion represents a bonding position to S or another divalent linking group represented by any one of Formulae L-1 to L-15, * represents a bonding position to T or another divalent linking group represented by any one of Formulae L-1 to L-15, m in Formula L-13 represents an integer of 0 to 4, m in Formulae L-14 and L-15 represents an integer of 0 to 2, R"s in Formulae L-1 and L-2 each independently represent a hydrogen atom or a substituent, and R"'s in Formulae L-13, L-14, and L-15 each independently represent a substituent.

In a case where L represents a divalent linking group obtained by bonding two or more divalent linking groups represented by any one of Formulae L-1 to L-15, * of one linking group is bonded to a wavy line portion of another linking group.

A bonding position of R' in Formulae L-13 to L-15 and a bonding position * on a T side can be at arbitrary positions on an aromatic ring or a hetero aromatic ring.

The bonding position * on the T side in Formula L-13 can be at an arbitrary position on an aromatic ring.

R' in Formulae L-1 and L-2 is preferably a hydrogen atom, a halogen atom, or an alkyl group and more preferably a hydrogen atom.

m in Formulae L-13 to L-15 is preferably 0 or 1 and more preferably 0.

As R" in Formulae L-13 to L-15, a halogen atom, an alkyl group, an alkynyl group, an alkenyl group, an alkoxy group, an alkylthio group, or an aryl group is preferable.

L is preferably a divalent linking group represented by any one of Formulae L-1 to L-4 and L-13 to L-15 or a divalent linking group obtained by bonding two or more divalent linking groups represented by any one of Formulae L-1 to L-4 and L-13 to L-15, more preferably a divalent linking group represented by any one of Formulae L-1 to L-4 and L-13 to L-15 singly, and even more preferably a divalent linking group represented by any one of Formulae L-1, L-3, and L-15 singly.

T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is 2 or greater, a siloxane group, an oligosiloxane group having two or more silicon atoms, or a trialkylsilyl group, preferably represents an alkyl group, a vinyl group, or an ethynyl group, more preferably represents an alkyl group, even more preferably represents an alkyl group having 5 to 19 carbon atoms, and particularly preferably represents an alkyl group having 7 to 13 carbon atoms.

An alkyl group in T is preferably a linear alkyl group.

In the group represented by Formula W above, a sum of the numbers of carbon atoms is preferably 2 or greater, more preferably 4 or greater, even more preferably 5 or greater, and particularly preferably 8 or greater. The sum of the numbers of carbon atoms is preferably 40 or less, more preferably 30 or less, and even more preferably 20 or less. In the aforementioned aspect, solution process suitability is excellent, and carrier mobility of the obtained organic semiconductor film is more excellent.

In the group represented by Formula W above, it is preferable that L represents a methylene group, and T represents an alkyl group. That is, the group represented by Formula W above is preferably an alkyl group, more preferably an alkyl group having 2 or more carbon atoms, even more preferably an alkyl group having 4 or more carbon atoms, particularly preferably an alkyl group having 5 or more carbon atoms, and most preferably an alkyl group having 8 or more carbon atoms. The group represented by Formula W above is more preferably an alkyl group having 40 or less carbon atoms, even more preferably an alkyl group having 30 or less carbon atoms, and particularly preferably an alkyl group having 20 or less carbon atoms. In the aforementioned aspect, solution process suitability is more excellent, and the carrier mobility of the obtained organic semiconductor film is more excellent.

The specific compound is preferably a point symmetric compound and more preferably point symmetric about a point A below.

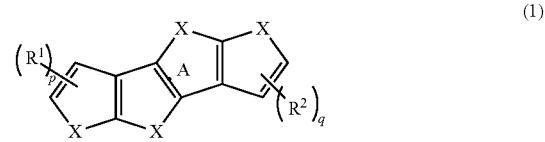

In the formula, p and q are the same as those in Formula 1 above, and each represent an integer of 0 to 2. $R^1$ and $R^2$ are the same as those in Formula 1 above and each represent a halogen atom or the group represented by Formula W.

It is preferable that $R^1$ and $R^2$ each represent an alkyl group having 4 to 18 carbon atoms or the group represented by Formula W, and p=1 and q=0 are satisfied. It is more preferable that $R^1$ and $R^2$ each represent an alkyl group having 4 to 18 carbon atoms or the group represented by Formula W (S represents a single bond, L represents (L-2), (L-3), (L-14), or (L-15), and T represents an alkyl group having 4 to 18 carbon atoms), and p=q=1 is satisfied.

It is preferable that the specific compound is point symmetric about the point A above, since carrier mobility of an obtained organic semiconductor film is more excellent.

Specific examples of the compound represented by Formula 1 include compounds provided below. However, it is obvious that the invention is not limited thereto.

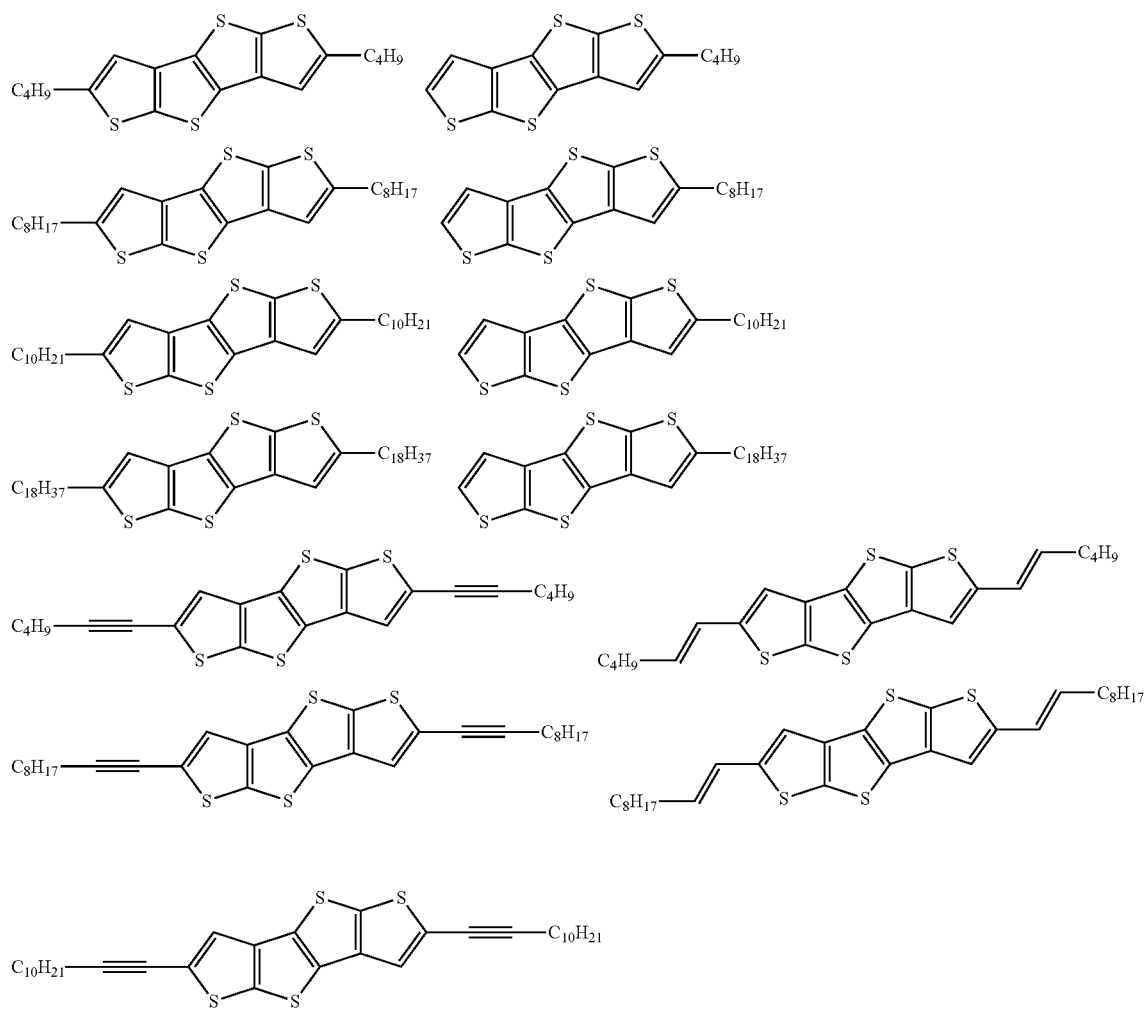

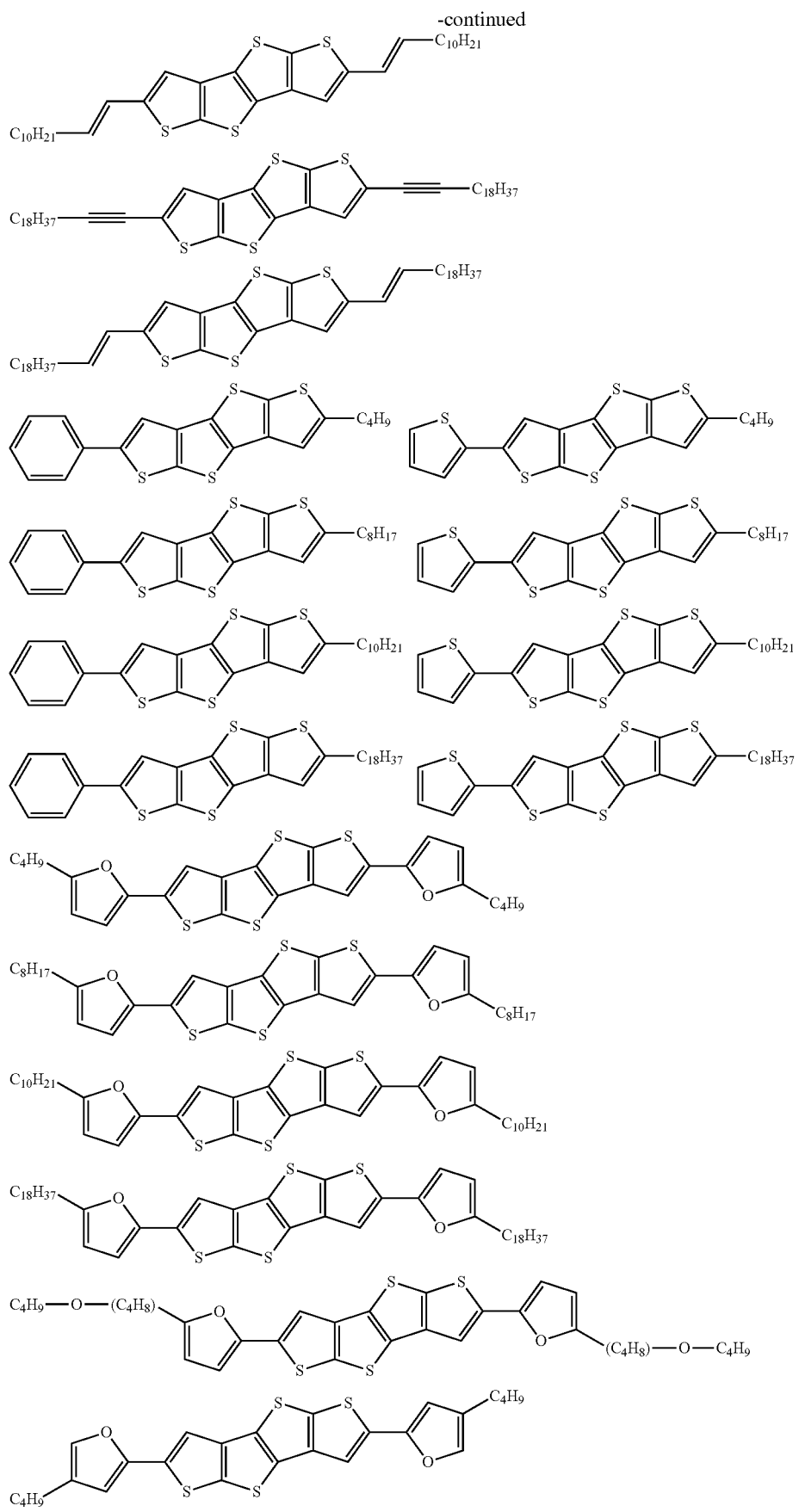

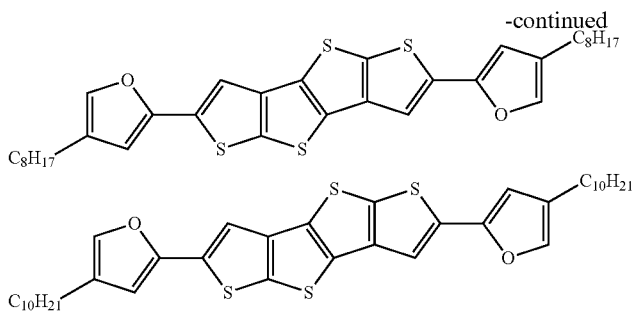

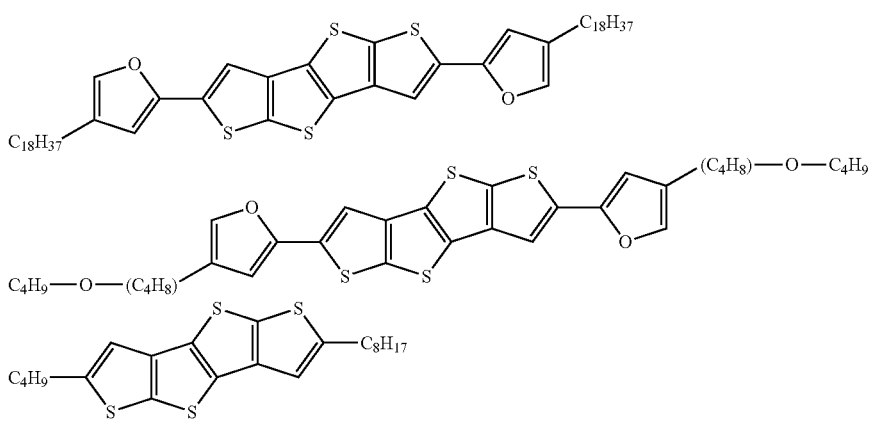

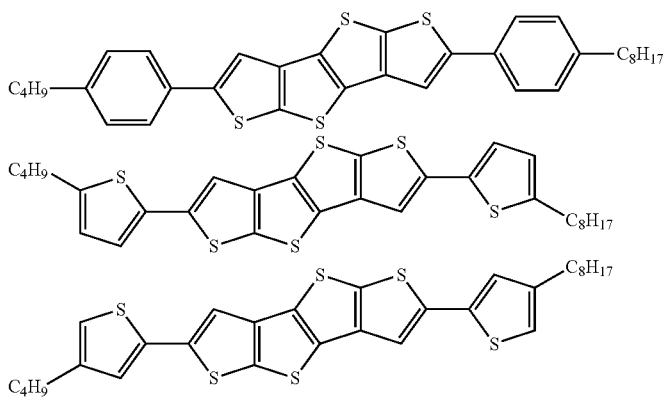

A method of synthesizing the compound represented by Formula 1 is not particularly limited. However, the compound represented by Formula can be synthesized with reference to well-known methods (for example, methods disclosed in Kazuo Takimiya, Adv. Mater., 2011, 23, 4347-4370). Examples of the synthesis method include a method of introducing substituents ($R^1$ and $R^2$) by causing sodium sulfide, iodine, and copper iodide to act with a compound Z below or causing tertiary butyllithium and sulfur to act with each other in this order so as to halogenize the second position of an obtained thiophene tetracyclic fused ring compound and performing coupling reaction with an aryl-boronic acid, an organozinc reagent, or a Grignard compound by using a transition metal catalyst.

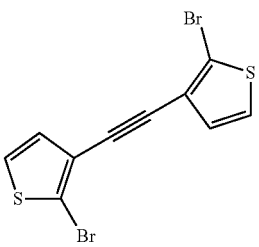

(Z)

The compound represented by Formula 1 may be used singly or two or more types thereof may be used in combination.

In the semiconductor active layer of the organic semiconductor element according to the present invention or an organic semiconductor film according to the present invention described below, a content of the compound represented by Formula 1 is preferably 30 to 100 mass %, more preferably 50 to 100 mass %, and even more preferably 70 to 100 mass %. In a case where a binder polymer described below is not contained, the total content is preferably 90 to 100 mass % and more preferably 95 to 100 mass %.

<Oligomer or polymer having constitutional repeating unit including structure represented by Formula 3>

The second organic semiconductor element according to the present invention includes an oligomer or a polymer (specific polymer compound) having a constitutional repeating unit including a structure represented by Formula 3 above in a semiconductor active layer.

The specific polymer compound is an organic semiconductor compound.

The specific polymer compound may have a constitutional repeating unit consisting of only the structure represented by Formula 3. In addition to the structure represented by Formula 3, a constitutional repeating unit including another structure may be included, and the invention is not particularly limited to this.

In Formula 3, $X^3$ represents a chalcogen atom (an O atom, a S atom, a Se atom, and a Te atom), preferably represents a S atom or a Se atom, and more preferably represents a S atom. In the aforementioned aspect, carrier mobility of an obtained organic semiconductor film is more excellent.

$R^{31}$ and $R^{32}$ each independently represent a halogen atom or a group represented by Formula W below, and a group represented by Formula W below is preferable. In the aforementioned aspect, carrier mobility of the obtained organic semiconductor film is more excellent.

—S-L-T  (W)

S represents a single bond or $—(C(R^S)_2)_n—$ and preferably represents a single bond.

$R^S$'s each independently represent a hydrogen atom or a halogen atom, and preferably represent a hydrogen atom.

n represents an integer of 1 to 17, preferably an integer of 1 to 8, and more preferably an integer of 1 to 4.

In view of coating film formability and heat resistance of an obtained organic semiconductor film, $R^1$ and $R^2$ are preferably the same groups.

The number of carbon atoms of $R^1$ is preferably 5 to 40 and more preferably 8 to 20.

The number of carbon atoms of $R^2$ is preferably 5 to 40 and more preferably 8 to 20.

L represents a single bond, a divalent linking group represented by any one of Formulae L-1 to L-15 below, or a divalent linking group obtained by bonding two or more divalent linking groups represented by any one of Formulae L-1 to L-15 below.

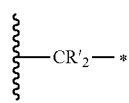

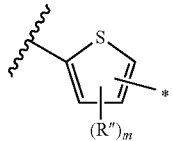
(L-15)

In Formulae L-1 to L-15, a wavy line portion represents a bonding position to S or another divalent linking group represented by any one of Formulae L-1 to L-15, * represents a bonding position to T or another divalent linking group represented by any one of Formulae L-1 to L-15, m in Formula L-13 represents an integer of 0 to 4, m in Formulae L-14 and L-15 represents an integer of 0 to 2, R"s in Formulae L-1 and L-2 each independently represent a hydrogen atom or a substituent, and R'"s in Formulae L-13, L-14, and L-15 each independently represent a substituent.

In a case where L represents a divalent linking group obtained by bonding two or more divalent linking groups represented by any one of Formulae L-1 to L-15, * of one linking group is bonded to a wavy line portion of another linking group.

A bonding position of R' in Formulae L-13 to L-15 and a bonding position * on the T side can be at arbitrary positions on an aromatic ring or a hetero aromatic ring. In a case of a thiophene ring, a fourth position or a fifth position is preferable, and in case of a furan ring, a fourth position or a fifth position is preferable, and m=0 is preferable.

The bonding position * on the T side in Formula L-13 can be at an arbitrary position on an aromatic ring.

R' in Formulae L-1 and L-2 is preferably a hydrogen atom, a halogen atom, or an alkyl group and more preferably a hydrogen atom.

m in Formulae L-13 to L-15 is preferably 0 or 1 and preferably 0.

R" in Formulae L-13 to L-15 is preferably a halogen atom, an alkyl group, an alkynyl group, an alkenyl group, an alkoxy group, an alkylthio group, or an aryl group.

L preferably represents a divalent linking group represented by any one of Formulae L-1 to L-4 and L-13 to L-15 or a divalent linking group obtained by bonding two or more divalent linking groups represented by any one of Formulae L-1 to L-4 and L-13 to L-15 and more preferably a divalent linking group represented by any one of Formulae L-1 to L-4 and L-13 to L-15 singly.

T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is 2 or greater, a siloxane group, an oligosiloxane group having two or more silicon atoms, or a trialkylsilyl group, preferably represents an alkyl group, a vinyl group, or an ethynyl group, more preferably an alkyl group, even more preferably an alkyl group having 5 to 19 carbon atoms, and particularly preferably an alkyl group having 7 to 13 carbon atoms.

An alkyl group in T is preferably a linear alkyl group.

In the group represented by Formula W above, a sum of the numbers of carbon atoms is preferably 2 or greater, more preferably 4 or greater, even more preferably 5 or greater, and particularly preferably 8 or greater. A sum of the numbers of carbon atoms is preferably 40 or less, more preferably 30 or less, and even more preferably 20 or less. In the aforementioned aspect, solution process suitability is more excellent, and carrier mobility of the obtained organic semiconductor film is more excellent.

In the group represented by Formula W above, it is preferable that L represents a methylene group, and T represents an alkyl group. That is, the group represented by Formula W above is preferably an alkyl group, preferably an alkyl group having 2 or more carbon atoms, more preferably an alkyl group having 4 or more carbon atoms, even more preferably an alkyl group having 5 or more carbon atoms, and particularly preferably an alkyl group having 8 or more carbon atoms. An alkyl group having 40 or less carbon atoms is preferable, an alkyl group having 30 or less carbon atoms is more preferable, and an alkyl group having 20 or less carbon atoms is even more preferable. In the aforementioned aspect, solution process suitability is more excellent, and carrier mobility of the obtained organic semiconductor film is more excellent.

The structure represented by Formula 3 is preferably a structure of point symmetric and more preferably point symmetric about a point A below.

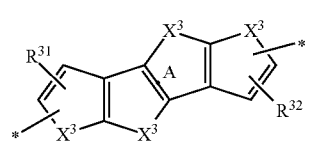
(3)

In Formula 3, $X^3$'s each independently represent a chalcogen atom, $R^{31}$ and $R^{32}$ each independently represent a hydrogen atom, a halogen atom, or a substituent represented by Formula W below, and * represents a bonding position.

—S-L-T    (W)

In Formula W, S represents a single bond or —(C($R^S$)$_2$)$_n$—, $R^S$'s each independently represent a hydrogen atom or a halogen atom, n represents an integer of 1 to 17, L represents a single bond, a divalent linking group represented by any one of Formulae L-1 to L-15 above, or a divalent linking group obtained by bonding two or more divalent linking groups represented by any one of Formulae L-1 to L-15 above, and T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is 2 or greater, a siloxane group, an oligosiloxane group having two or more silicon atoms, or a trialkylsilyl group.

It is preferable that the structure represented by Formula 3 is point symmetric about the point A, since carrier mobility of the obtained organic semiconductor film is more excellent.

The specific polymer compound is preferably conjugated in a main chain direction. Here, the main chain direction is a direction of bonding a constitutional repeating unit. If the specific polymer compound is conjugated in a main chain direction, charge transporting properties in a main chain is excellent, and thus high mobility can be obtained.

In addition to the structure represented by Formula 3, in the constitutional repeating unit, the specific polymer compound preferably further includes a structure represented by Formula Z below.

—Ar$^1$—(V)$_p$—Ar$^2$—    (Z)

In Formula Z, Ar$^1$ and Ar$^2$ each independently represent a single bond, a vinylene group, an ethynylene group, an arylene group, a heteroarylene group, or a divalent group obtained by bonding two or more of these, V represents a single bond or a divalent conjugate group having 2 to 40 carbon atoms, p represents 1 to 6, and when there are two or more p's, two or more V's may be identical to each other. Here, all of $Ar^1$, $Ar^2$, and V are not single bonds at the same time.

That is, the specific polymer compound preferably has a constitutional repeating unit represented by Formula 3-1 below and more preferably has a constitutional repeating unit represented by Formula 3-2.

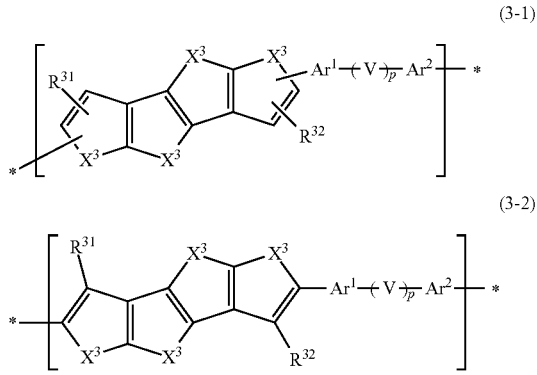

(3-1)

(3-2)

In Formulae 3-1 and 3-2 above, $R^{31}$, $R^{32}$, and $X^3$ respectively are the same as $R^{31}$, $R^{32}$, and $X^3$ in Formula 3 above, and preferable ranges thereof are also the same. $Ar^1$, $Ar^2$, V, and p are the same as $Ar^1$, $Ar^2$, V, and p in Formula Z above, and preferable ranges thereof are also the same.

In Formula Z, the arylene group represented by $Ar^1$ and $Ar^2$ is preferably an arylene group having 6 to 20 carbon atoms and more preferably an arylene group having 6 to 14 carbon atoms. Specifically, a group obtained by removing two hydrogen atoms from benzene, naphthalene, anthracene, phenanthrene, triphenylene, pyrene, chrysene, tetracene, pentaphene, and pentacene is preferable, and a group obtained by removing two hydrogen atoms from benzene, naphthalene, and anthracene is more preferable.

In Formula Z, a heteroatom included in a heteroarylene group represented by $Ar^1$ and $Ar^2$ is preferably a sulfur atom (S), an oxygen atom (O), a nitrogen atom (N), a selenium atom (Se), or a silicon atom (Si), more preferably a sulfur atom, a nitrogen atom, or an oxygen atom, even more preferably a sulfur atom or a nitrogen atom, and particularly preferably a sulfur atom.

Specific examples of the heteroarylene group include a group obtained by removing two hydrogen atoms from thiophene, furan, pyran, pyrrole, pyridine, pyrazine, pyrimidine, pyridazine, selenophene, and imidazole. The heteroarylene group is preferably a group obtained by removing two hydrogen atoms from thiophene, selenophene, or pyrrole, more preferably a group obtained by removing two hydrogen atoms from thiophene or furan, and even more preferably a group obtained by removing two hydrogen atoms from thiophene.

An arylene group and a heteroarylene group represented by $Ar^1$ and $Ar^2$ may have a substituent. Examples of the substituent preferably include a halogen atom, an alkyl group (preferably having 1 to 40 carbon atoms and more preferably having 4 to 20 carbon atoms), an alkenyl group (preferably having 2 to 40 carbon atoms and more preferably having 4 to 20 carbon atoms), and an alkynyl group (preferably having 2 to 40 carbon atoms and more preferably having 4 to 20 carbon atoms), and the alkyl group, the alkenyl group, and the alkynyl group may be further substituted with a halogen atom, an alkoxy group, or the like.

In a case where $Ar^1$ and $Ar^2$ each represent a divalent group obtained by bonding two or more groups selected from the group consisting of a vinylene group, an ethynylene group, an arylene group, and a heteroarylene group, $Ar^1$ and $Ar^2$ each may be a divalent group obtained by linking two or more of the same groups or a divalent group obtained by bonding two or more of different groups. The invention is not particularly limited. However, a divalent group obtained by linking two or more of the same groups is preferable, and a divalent group obtained by linking two or more arylene groups or two or more heteroarylene groups is more preferable.

$Ar^1$ and $Ar^2$ each independently and preferably represent a single bond or a divalent linking group represented by Formula Ar-1 or Formula Ar-2 below and more preferably a single bond or a divalent linking group represented by Formula Ar-1 below.

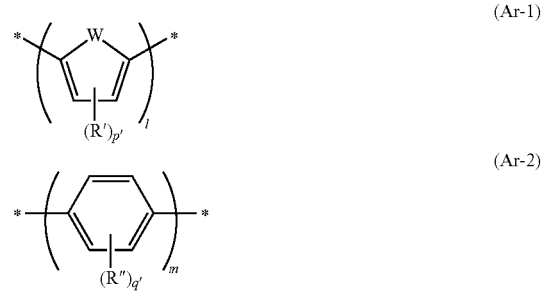

(Ar-1)

(Ar-2)

In Formula Ar-1, R"s each independently represent an alkyl group, p' represents an integer of 0 to 2, R"s adjacent to each other may form a ring, W represents a chalcogen atom, and l represents an integer of 1 to 4.

In Formula Ar-2, R'''s each independently represent an alkyl group or an alkoxy group, q' represents an integer of 0 to 4, R'''s adjacent to each other may form a ring, and m represents an integer of 1 to 4.

In Formula Ar-1, an alkyl group represented by R' is preferably an alkyl group having 1 to 40 carbon atoms and more preferably an alkyl group having 4 to 20 carbon atoms. In Formula Ar-1, p' represents an integer of 0 to 2, preferably 0 or 1, and more preferably 1. When p' is 2, two R"s may be identical to or different from each other, and may be bonded to each other to form a ring. In Formula Ar-1, W represents a chalcogen atom (an O atom, a S atom, a Se atom, and a Te atom), preferably represents a S atom or a Se atom, and more preferably represents a S atom. In the aforementioned aspect, carrier mobility of an obtained organic semiconductor film is more excellent.

In Formula Ar-2, an alkyl group represented by R" is preferably an alkyl group having 1 to 40 carbon atoms, and more preferably an alkyl group having 4 to 20 carbon atoms. An alkoxy group represented by R" is preferably an alkoxy group having 1 to 40 carbon atoms and more preferably an alkoxy group having 1 to 20 carbon atoms.

In Formula Ar-2, q' represents an integer of 0 to 4, more preferably an integer of 0 to 3, even more preferably an integer of 0 to 2, and particularly preferably 0 or 1.

In Formulae Ar-1 and Ar-2, l and m each represent an integer of 1 to 4, preferably an integer of 1 to 3, more preferably 1 or 2, and even more preferably 1.

In Formula Z, V represents a single bond or a divalent conjugate group having 2 to 40 carbon atoms.

V is preferably a divalent linking group selected from the group consisting of Formulae $V_D$-1 to $V_D$-16 and $V_A$-1 to $V_A$-11 below. All of these are divalent conjugate groups.

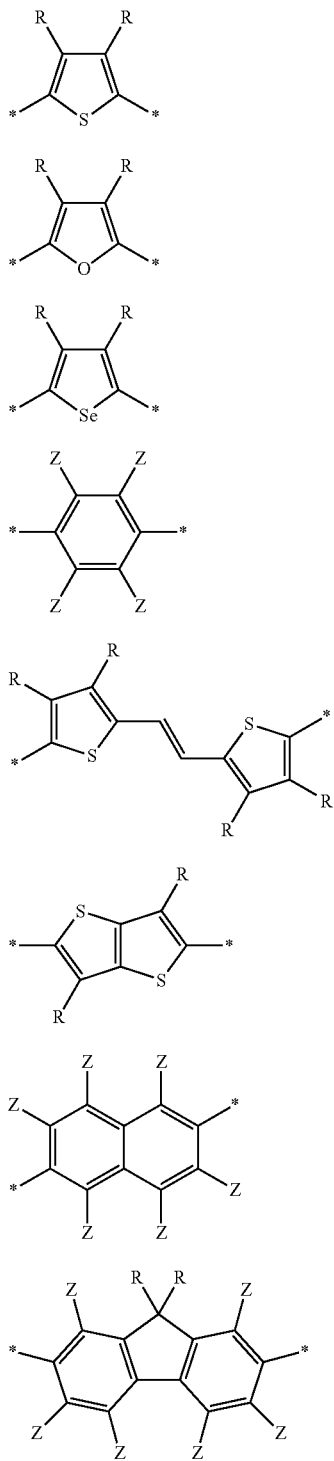

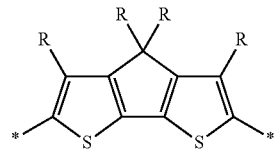

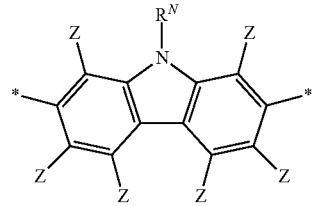

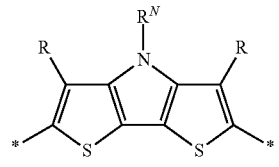

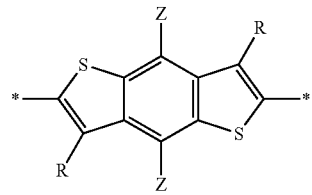

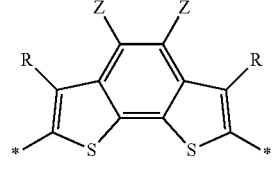

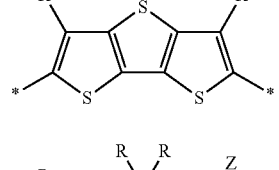

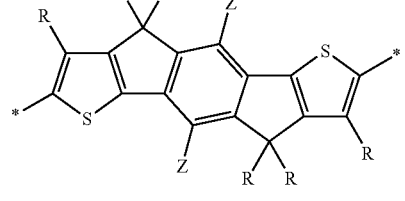

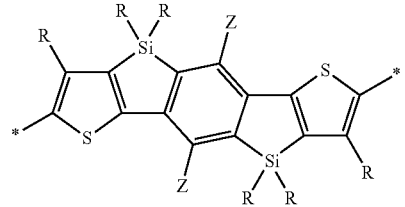

-continued (V_A-1) 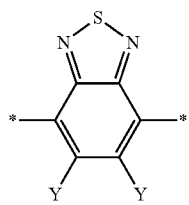

(V_A-2) 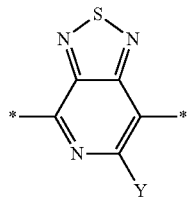

(V_A-3) 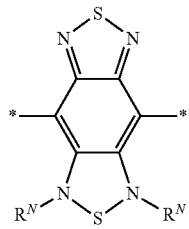

(V_A-4) 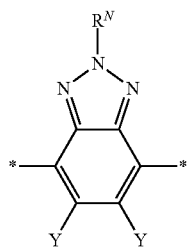

(V_A-5) 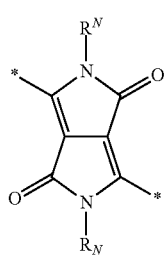

(V_A-6) 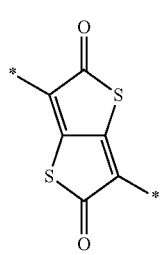

-continued (V_A-7) 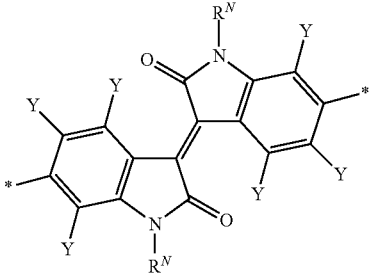

(V_A-8) 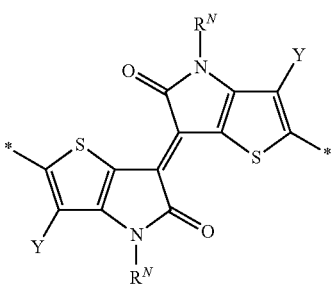

(V_A-9) 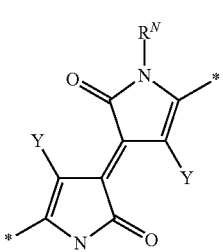

(V_A-10) 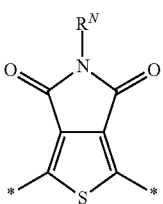

(V_A-11) 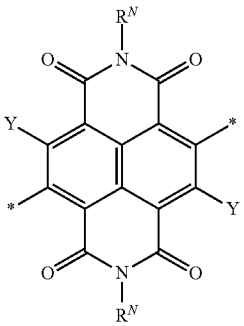

R's in Formulae $V_D$-1 to $V_D$-3, $V_D$-5, $V_D$-6, $V_D$-8, $V_D$-9, and $V_D$-11 to $V_D$-16 each independently represent a hydrogen atom, a halogen atom, an alkyl group, and R's adjacent to each other are bonded to each other to form a ring, Z's in Formulae $V_D$-4, $V_D$-7, $V_D$-8, $V_D$-10, $V_D$-12, $V_D$-13, $V_D$-15, and $V_D$-16 each independently represent a hydrogen atom, a halogen atom, an alkyl group, or an alkoxy group, and Z's adjacent to each other may be bonded to each other to form a ring, $R^N$'s in Formulae $V_D$-10, $V_D$-11, $V_A$-3, $V_A$-4, $V_A$-5, and $V_A$-7 to $V_A$-11 each independently represent an alkyl group, and $R^N$'s adjacent to each other may be bonded to each other to form a ring, and Y's in Formulae $V_A$-1, $V_A$-2, $V_A$-4, $V_A$-7 to $V_A$-9, and $V_A$-11 each independently represent a hydrogen atom, an alkyl group, an alkoxy group, CN, or a halogen atom, and Y's adjacent to each other may be bonded to each other to form a ring.

An alkyl group represented by R in Formulae $V_D$-1 to $V_D$-3, $V_D$-5, $V_D$-6, $V_D$-8, $V_D$-9, and $V_D$-11 to $V_D$-16 is preferably an alkyl group having 1 to 40 carbon atoms and more preferably an alkyl group having 4 to 20 carbon atoms.

An alkyl group represented by Z in Formulae $V_D$-4, $V_D$-7, $V_D$-8, $V_D$-10, $V_D$-12, $V_D$-13, $V_D$-15, and $V_D$-16 is preferably an alkyl group having 1 to 40 carbon atoms and more preferably an alkyl group having 1 to 20 carbon atoms. The alkoxy group represented by Z is preferably an alkoxy group having 1 to 40 carbon atoms and more preferably an alkoxy group having 1 to 20 carbon atoms.

An alkyl group represented by $R^N$ in Formulae $V_D$-10, $V_D$-11, $V_A$-3, $V_A$-4, $V_A$-5, and $V_A$-7 to $V_A$-11 is preferably an alkyl group having 1 to 40 carbon atoms and more preferably an alkyl group having 1 to 20 carbon atoms. $R^N$ preferably represents an alkyl group.

In Formulae $V_A$-1, $V_A$-2, $V_A$-4, $V_A$-7 to $V_A$-9, and $V_A$-11, an alkyl group represented by Y is preferably an alkyl group having 1 to 40 carbon atoms and more preferably an alkyl group having 1 to 20 carbon atoms. The alkoxy group is preferably an alkoxy group having 1 to 40 carbon atoms and more preferably an alkoxy group having 1 to 20 carbon atoms. As Y, a hydrogen atom, a fluorine atom, or a cyano group is preferable.

Examples of the halogen atoms represented by R, Z, $R^N$, and Y above include a fluorine atom, a chlorine atom, a bromine atom, and an iodine atom. Among these, a fluorine atom or a chlorine atom is preferable, and a fluorine atom is more preferable.

Among these, V preferably represents a divalent group selected from the group consisting of Formulae $V_A$-1 to $V_A$-11 and more preferably a divalent linking group selected from the group consisting of Formulae $V_A$-1, $V_A$-5, and $V_A$-7.

p represents an integer of 1 to 6. In a case where p represents an integer of 2 to 6, plural V's may be identical to or different from each other, and the invention is not particularly limited thereto.

p is preferably an integer of 1 to 4, more preferably an integer of 1 to 3, even more preferably 1 or 2, and particularly preferably 1.

In the specific polymer compound, the content of the constitutional repeating unit including the structure represented by Formula 3 is preferably 60 to 100 mass %, more preferably 80 to 100 mass %, and even more preferably 90 to 100 mass % with respect to a total mass of the specific polymer compound. It is particularly preferable that the constitutional repeating unit is substantially formed only from a constitutional repeating unit including the structure represented by Formula 3. The expression "being substantially formed only from a constitutional repeating unit including a structure represented by Formula 3" means that a content of the constitutional repeating unit of the structure represented by Formula 3 is 95 mass % or greater, preferably 97 mass % or greater, and more preferably 99 mass % or greater.

If the content of the constitutional repeating unit including the structure represented by Formula 3 is in the range described above, an organic semiconductor having excellent mobility can be obtained.

As described above, the constitutional repeating unit including the structure represented by Formula 3 is preferably a constitutional repeating unit represented by Formula 3-1 and more preferably a constitutional repeating unit represented by Formula 3-2.

The specific polymer compound is a compound having two or more constitutional repeating units including a structure represented by Formula 3 and may be an oligomer in which the number "n" of constitutional repeating units is two to nine or may be a polymer in which the number "n" of constitutional repeating units is 10 or greater. Among these, a polymer in which the number "n" of constitutional repeating units is 10 or greater is preferable, in view of mobility and obtainable physical properties of the organic semiconductor film.

A number-average molecular weight of the specific polymer compound is not particularly limited. However, the number-average molecular weight is preferably 1,000 or greater, more preferably 10,000 or greater, even more preferably 20,000 or greater, particularly preferably 30,000 or greater, and most preferably 50,000 or greater. The number-average molecular weight is preferably 2,500,000 or less, more preferably 2,000,000 or less, even more preferably 1,500,000 or less, particularly preferably 1,000,000 or less, and most preferably 500,000 or less.

If the number-average molecular weight is in the range above, solubility of the solvent and the film quality stability are compatible with each other.

According to the present invention, a weight-average molecular weight and a number-average molecular weight are measured by a gel permeation chromatography method (GPC method) and can be obtained in terms of standard polystyrene. Specifically, for example, HLC-8220GPC (manufactured by manufactured by Tosoh Corporation) is used as GPC, three of TSKgeL SuperHZM-H, TSKgeL SuperHZ4000, TSKgeL SuperHZ2000 (manufactured by Tosoh Corporation, 4.6 mmID×15 cm) are used as columns, and THF (tetrahydrofuran) is used as an eluent. As the condition, the sample concentration is set as 0.35 mass %, a flow rate is set as 0.35 ml/min, a sample injection volume is set as 10 μl, a measurement temperature is set as 40° C., and an IR detector was used. A calibration curve is manufactured from eight samples of "standard sample TSK standard, polystyrene": "F-40", "F-20", "F-4", "F-1", "A-5000", "A-2500", "A-1000", and "n-propylbenzene" manufactured by Tosoh Corporation.

In an organic semiconductor layer described below, and an organic semiconductor film or a composition for forming an organic semiconductor film described below, only one specific polymer compound may be included, and two or more types of the specific polymer compounds may be included. However, in view of alignment, only one type is preferable.

According to the present invention, it is obvious that an aspect in which a specific compound and a specific polymer compound are used together in an organic semiconductor layer is not excluded.

Specific examples of the specific polymer compound include compounds provided below, but it is obvious that the invention is not limited thereto.

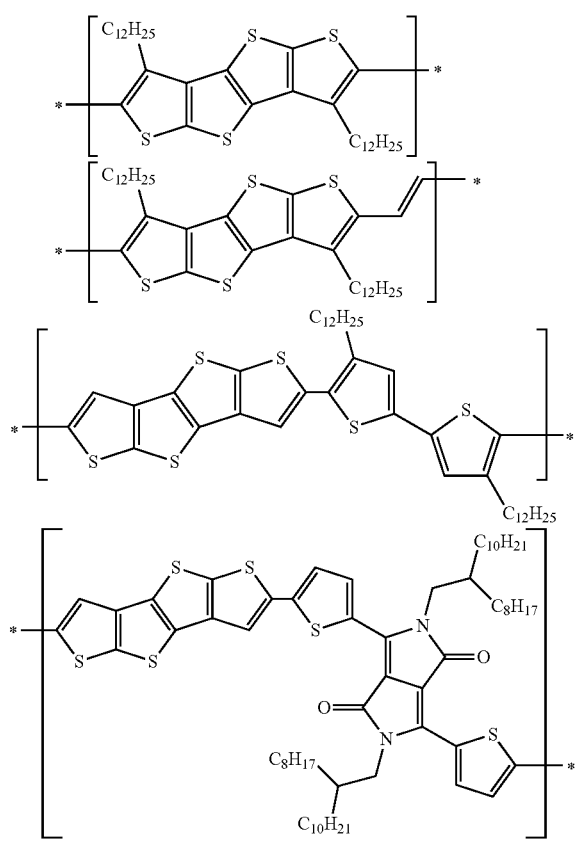

In the formula, * represents a bonding position.

A method of synthesizing a specific polymer compound is not particularly limited, and the specific polymer compound can be synthesized with reference to well-known methods. Examples of the synthesis method include a method of polymerizing dihalide of a fused polycyclic aromatic ring compound and a bistrialkylstannyl compound by Stille coupling reaction.

The specific polymer compound may be used singly or two or more types thereof may be used in combination.

In the semiconductor active layer of the organic semiconductor element according to the present invention or the organic semiconductor film according to the present invention described below, the content of the specific polymer compound preferably 30 to 100 mass %, more preferably 50 to 100 mass %, and even more preferably 70 to 100 mass %. In a case where a binder polymer described below is not contained, the total content is preferably 90 to 100 mass % and more preferably 95 to 100 mass %.

<Binder Polymer>

A semiconductor active layer of a first organic semiconductor element according to the present invention and a semiconductor active layer of a second organic semiconductor each preferably contain a binder polymer.

The first and second organic semiconductor elements according to the present invention each may be an organic semiconductor element having the semiconductor active layer and a layer including a binder polymer.

The types of the binder polymer are not particularly limited, and well-known binder polymers can be used.

Examples of the binder polymer include a polystyrene resin, an acrylic resin, rubber, and a thermoplastic elastomer.

Among these, as the binder polymer, a polymer compound (a polymer having a monomer unit having a benzene ring group) having a benzene ring is preferable. The content of the monomer unit having a benzene ring group is not particularly limited. However, the content is preferably 50 mol % or greater, more preferably 70 mol % or greater, and even more preferably 90 mol % or greater with respect to the entire monomer unit. The upper limit is not particularly limited, but examples of the upper limit include 100 mol %.

Examples of the binder polymer include polystyrene, poly(a-methylstyrene), polyvinyl cinnamate, poly(4-vinylphenyl), and poly(4-methylstyrene).

A weight-average molecular weight of the binder polymer is not particularly limited, but is preferably 1,000 to 2,000,000, more preferably 3,000 to 1,000,000, and even more preferably 5,000 to 600,000.

In a case where a solvent described below is used, it is preferable that the binder polymer exhibits solubility higher than the solubility of the compound represented by Formula 1 in a used solvent. If the above aspect is adopted, mobility and heat resistance of the obtained organic semiconductor are further improved.

A content of the binder polymer in the semiconductor active layer of the organic semiconductor element of the present invention is preferably 1 to 200 parts by mass, more preferably 10 to 150 parts by mass, and even more preferably 20 to 120 parts by mass with respect to 100 parts by mass of the content of the compound represented by Formula 1. If the content is within the above range, mobility and heat resistance of the obtained organic semiconductor are further improved.

<Other Components>

Other components may be included other than the specific compound or the specific polymer compound and the binder polymer may be included in the semiconductor active layer according to the first and second organic semiconductor element of the present invention.

As other components, known additives and the like can be used.

In the semiconductor active layer, a content of the components other than the specific compound or the specific polymer compound and the binder polymer is preferably 10 mass % or less, more preferably 5 mass % or less, even more preferably 1 mass % or less, and particularly preferably 0.1 mass % or less. If the content of other components is within the above range, film formability is improved, and mobility and heat resistance of the obtained organic semiconductor are further improved.

The method of forming the semiconductor active layer according to the organic semiconductor element of the present invention is not particularly limited. However, a desired semiconductor active layer can be formed by applying the organic semiconductor composition according to the present invention described below to a source electrode, a drain electrode, and a gate insulating film and performing a drying treatment, if necessary.

The organic semiconductor element of the present invention is preferably manufactured using the organic semiconductor composition of the present invention described below.

A method of manufacturing an organic semiconductor film or an organic semiconductor element by using the organic semiconductor composition of the present invention is not particularly limited, and known methods can be adopted. The organic semiconductor film is preferably manufactured by a solution coating method, and examples thereof include a method of manufacturing an organic semiconductor film by applying the composition onto a predetermined base material and if necessary, performing a drying treatment.

The method of applying the composition onto a base material is not particularly limited, and known methods can be adopted. Examples thereof include an ink jet printing method, a screen printing method, a flexographic printing method, a bar coating method, a spin coating method, a knife coating method, a doctor blade method, and the like. Among these, an ink jet printing method, a screen printing method, and a flexographic printing method are preferable.

Preferred examples of the flexographic printing method include an aspect in which a photosensitive resin plate is used as a flexographic printing plate. By printing the composition onto a substrate according to the aspect, a pattern can be easily formed.

Among the above methods, the method of manufacturing an organic semiconductor element of the present invention preferably includes a coating step of coating a substrate with the organic semiconductor composition of the present invention described below. The method of manufacturing an organic semiconductor element of the present invention more preferably includes a coating step of coating a substrate with the organic semiconductor composition of the present invention and a removing step of removing at least a portion of the solvent from the coated semiconductor composition.

The organic semiconductor composition according to the present invention described below preferably includes a solvent and more preferably includes a solvent having a boiling point of 100° C. or higher.

As the solvent, well-known solvents can be used.

Specifically, examples thereof include a hydrocarbon-based solvent such as hexane, octane, decane, toluene, xylene, mesitylene, ethylbenzene, decalin, and 1-methylnaphthalene, a ketone-based solvent such as acetone, methyl ethyl ketone, methyl isobutyl ketone, or cyclohexanone, a halogenated hydrocarbon-based solvent such as dichloromethane, chloroform, tetrachloromethane, di chl oroethane, trichloroethane, tetrachloroethane, chlorobenzene, dichlorobenzene, and chlorotoluene, an ester-based solvent such as ethyl acetate, butyl acetate, and amyl acetate, an alcohol-based solvent such as methanol, propanol, butanol, pentanol, hexanol, cyclohexanol, methyl cellosolve, ethyl cellosolve, and ethylene glycol, an ether-based solvent such as dibutyl ether, tetrahydrofuran, dioxane, and anisole, an amide-based solvent such as N,N-dimethylformamide and N,N-dimethylacetamide, an imide-based solvent such as 1-methyl-2-pyrrolidone and 1-methyl-2-imidazolidinone, a sulfoxide-based solvent such as dimethylsulfoxide, and a nitrile-based solvent such as acetonitrile.

In order to obtain stability of an organic semiconductor composition described below and to form an even film, a boiling point of the solvent in normal pressure is preferably 100° C. or higher, more preferably 150° C. or higher, even more preferably 175° C. or higher, and particularly preferably 200° C. or higher.

In order to dry the solvent, after the organic semiconductor composition is applied, the boiling point of the solvent in normal pressure is preferably 300° C. or lower, more preferably 250° C. or lower, and even more preferably 220° C. or lower.

Unless described otherwise, according to the present invention, the boiling point is a boiling point in normal pressure.

The solvent may be used singly or two or more types thereof may be used in combination.

Among these, a hydrocarbon-based solvent, a halogenated hydrocarbon-based solvent, and/or an ether-based solvent are preferable, and toluene, xylene, mesitylene, tetralin, dichlorobenzene and anisole are more preferable.

In a case where the solvent is contained, the content of the compound represented by in Formula 1 in the organic semiconductor composition of the present invention is preferably 20 mass % or less, more preferably 0.01 to 20 mass %, even more preferably 0.05 to 10 mass %, and particularly preferably 0.1 to 5 mass %. In a case where the binder polymer and the solvent are contained, the content of the binder polymer in the organic semiconductor composition according to the present invention is preferably 0.01 to 80 mass %, more preferably 0.05 to 10 mass %, and even more preferably 0.1 to 5 mass %. If the content is in the range described above, coating properties are excellent, and thus an organic semiconductor film can be easily formed.

The drying treatment in the removing step is a treatment performed if necessary, and the optimal treatment conditions are appropriately selected according to the type of the specific compound and the solvent used. In view of further improving mobility and heat resistance of the obtained organic semiconductor and improving productivity, a heating temperature is preferably 30° C. to 100° C. and more preferably 40° C. to 80° C., and a heating time is preferably 10 to 300 minutes and more preferably 30 to 180 minutes.

A thickness of the formed semiconductor active layer is not particularly limited. From the viewpoint of mobility and heat resistance of the obtained organic semiconductor, the film thickness is preferably 10 to 500 nm and more preferably 30 to 200 nm.

The organic semiconductor element is not particularly limited, but is preferably an organic semiconductor element having 2 to 5 terminals, and more preferably an organic semiconductor element having 2 or 3 terminals.

It is preferable that the organic semiconductor element is not a photoelectric conversion element.

The organic semiconductor element according to the present invention is preferably a non-luminous organic semiconductor element.

Examples of a 2-terminal element include a rectifier diode, a constant voltage diode, a PIN diode, a Schottky barrier diode, a surge protection diode, a diac, a varistor, a tunnel diode, and the like.

Examples of a 3-terminal element include a bipolar transistor, a Darlington transistor, a field effect transistor, insulated gate bipolar transistor, a uni-junction transistor, a static induction transistor, a gate turn thyristor, a triac, a static induction thyristor, and the like.

Among these, a rectifier diode and transistors are preferable, and a field effect transistor is more preferable.

As the field effect transistor, an organic thin film transistor is preferable.

An aspect of the organic thin film transistor of the present invention will be described with reference to drawings.

FIG. 1 is a schematic cross-sectional view of an aspect of an organic semiconductor element (organic thin film transistor (organic TFT)) of the present invention.

In FIG. 1, an organic thin film transistor 100 comprises a substrate 10, a gate electrode 20 disposed on the substrate 10, a gate insulating film 30 covering the gate electrode 20, a source electrode 40 and a drain electrode 42 which contact a surface of the gate insulating film 30 that is on the side opposite to the gate electrode 20 side, an organic semiconductor film 50 covering a surface of the gate insulating film 30 between the source electrode 40 and the drain electrode 42, and a sealing layer 60 covering each member. The organic thin film transistor 100 is a bottom gate-bottom contact type organic thin film transistor.

In FIG. 1, the organic semiconductor film 50 corresponds to a film formed of the composition described above.

Hereinafter, the substrate, the gate electrode, the gate insulating film, the source electrode, the drain electrode, the sealing layer, and methods for forming each of these will be specifically described.

<Substrate>

The substrate plays a role of supporting the gate electrode, the source electrode, the drain electrode, and the like which will be described later.

The type of the substrate is not particularly limited, and examples thereof include a plastic substrate, a glass substrate, a ceramic substrate, and the like. Among these, from the viewpoint of applicability to each device and costs, a glass substrate or a plastic substrate is preferable.

Examples of materials of the plastic substrate include a thermosetting resin (for example, an epoxy resin, a phenol resin, a polyimide resin, or a polyester resin (for example, polyethylene terephthalate (PET) or polyethylene naphthalate (PEN)) and a thermoplastic resin (for example, a phenoxy resin, a polyethersulfone, polysulfone, or polyphenylene sulfone).

Examples of materials of the ceramic substrate include alumina, aluminum nitride, zirconia, silicon, silicon nitride, silicon carbide, and the like.

Examples of materials of the glass substrate include soda lime glass, potash glass, borosilicate glass, quartz glass, aluminosilicate glass, lead glass, and the like.

<Gate Electrode, Source Electrode, and Drain Electrode>

Examples of materials of the gate electrode, the source electrode, and the drain electrode include a metal such as gold (Au), silver, aluminum (Al), copper, chromium, nickel, cobalt, titanium, platinum, tantalum, magnesium, calcium, barium, or sodium; a conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium arsenide; a carbon material such as fullerene, carbon nanotubes, or graphite; and the like. Among these, a metal is preferable, and silver and aluminum are more preferable.

A thickness of each of the gate electrode, the source electrode, and the drain electrode is not particularly limited, but is preferably 20 to 200 nm.

A method of forming the gate electrode, the source electrode, and the drain electrode is not particularly limited, but examples thereof include a method of vacuum vapor-depositing or sputtering an electrode material onto a substrate, a method of coating a substrate with a composition for forming an electrode, a method of printing a composition for forming an electrode onto a substrate, and the like. Furthermore, in a case where the electrode is patterned, examples of the patterning method include a photolithography method; a printing method such as ink jet printing, screen printing, offset printing, or relief printing; a mask vapor deposition method; and the like.

<Gate Insulating Film>

Examples of materials of the gate insulating film include a polymer such as polymethyl methacrylate, polystyrene, polyvinylphenol, polyimide, polycarbonate, polyester, polyvinylalcohol, polyvinyl acetate, polyurethane, polysulfone, polybenzoxazole, polysilsesquioxane, an epoxy resin, or a phenol resin; an oxide such as silicon dioxide, aluminum oxide, or titanium oxide; a nitride such as silicon nitride; and the like. Among these materials, in view of the compatibility with the organic semiconductor film, a polymer is preferable.

In a case where a polymer is used as the material of the gate insulating film, it is preferable to use a cross-linking agent (for example, melamine) in combination. If the cross-linking agent is used in combination, the polymer is cross-linked, and durability of the formed gate insulating film is improved.

A film thickness of the gate insulating film is not particularly limited, but is preferably 100 to 1,000 nm.

A method of forming the gate insulating film is not particularly limited, but examples thereof include a method of coating a substrate, on which the gate electrode is formed, with a composition for forming a gate insulating film, a method of vapor-depositing or sputtering the material of the gate insulating film onto a substrate on which the gate electrode is formed, and the like. A method of coating the aforementioned substrate with the composition for forming a gate insulating film is not particularly limited, and it is possible to use a known method (a bar coating method, a spin coating method, a knife coating method, or a doctor blade method).

In a case where the gate insulating film is formed by coating the substrate with the composition for forming a gate insulating film, for the purpose of removing the solvent, causing cross-linking, or the like, the composition may be heated (baked) after coating.

<Binder Polymer Layer>

The organic semiconductor element of the present invention preferably has a layer of the aforementioned binder polymer between a layer containing the semiconductor active layer and an insulating film, and more preferably has the aforementioned binder polymer between the semiconductor active layer and the gate insulating film. A film thickness of the binder polymer layer is not particularly limited, but is preferably 20 to 500 nm. The binder polymer layer should be a layer containing the aforementioned polymer, and is preferably a layer composed of the aforementioned binder polymer.

A method of forming the binder polymer layer is not particularly limited, and a known method (a bar coating method, a spin coating method, a knife coating method, a doctor blade method, or an ink jet method) can be used.

In a case where the binder polymer layer is formed by performing coating by using a composition for forming a binder polymer layer, for the purpose of removing a solvent, causing cross-linking, or the like, the composition may be heated (baked) after coating.

The binder polymer layer is preferably a binder polymer layer that can be formed together with a semiconductor active layer from the organic semiconductor composition according to the present invention.

<Sealing Layer>

From the viewpoint of durability, the organic semiconductor element of the present invention preferably comprises a sealing layer as an outermost layer. In the sealing layer, a known sealant can be used.

A thickness of the sealing layer is not particularly limited, but is preferably 0.2 to 10 μm.

A method of forming the sealing layer is not particularly limited, but examples thereof include a method of coating a substrate, on which the gate electrode, the gate insulating film, the source electrode, the drain electrode, and the organic semiconductor film are formed, with a composition for forming a sealing layer, and the like. Specific examples of the method of coating the substrate with the composition for forming a sealing layer are the same as the examples of the method of coating the substrate with the composition for forming a gate insulating film. In a case where the organic semiconductor film is formed by coating the substrate with the composition for forming a sealing layer, for the purpose of removing the solvent, causing cross-linking, or the like, the composition may be heated (baked) after coating.

Figure 2:
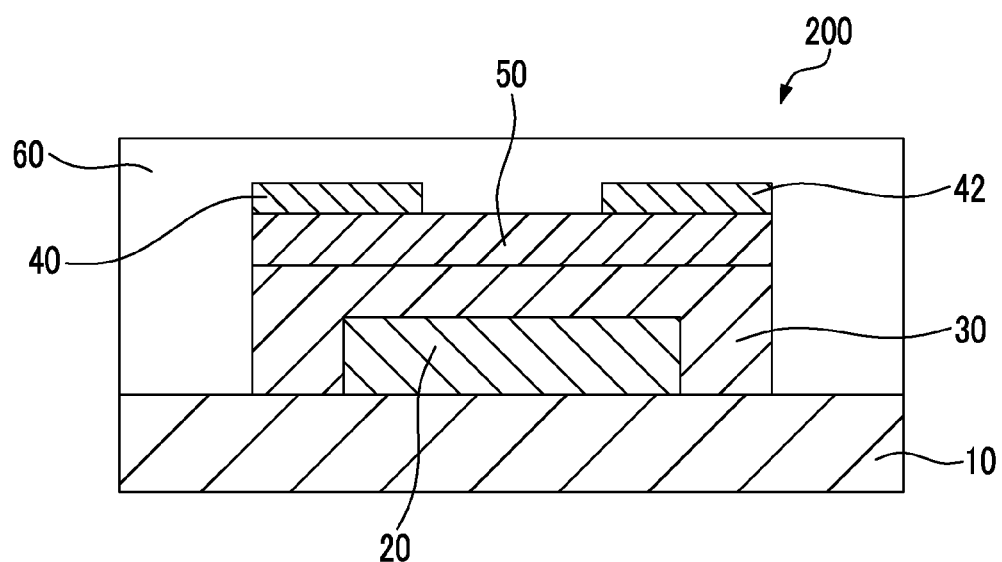
FIG. 2 is a schematic cross-sectional view of another aspect of the organic semiconductor element of the present invention.

FIG. 2 is a schematic cross-sectional view of another aspect of the organic semiconductor element (organic thin film transistor) of the present invention.

In FIG. 2, an organic thin film transistor 200 comprises the substrate 10, the gate electrode 20 disposed on the substrate 10, the gate insulating film 30 covering the gate electrode 20, the organic semiconductor film 50 disposed on the gate insulating film 30, the source electrode 40 and the drain electrode 42 disposed on the organic semiconductor film 50, and the sealing layer 60 covering each member. Herein, the source electrode 40 and the drain electrode 42 are formed using the aforementioned composition of the present invention. The organic thin film transistor 200 is a bottom gate-top contact type organic thin film transistor.

The substrate, the gate electrode, the gate insulating film, the source electrode, the drain electrode, the organic semiconductor film, and the sealing layer are as described above.

In FIGS. 1 and 2, the aspects of the bottom gate-bottom contact type organic thin film transistor and the bottom gate-top contact type organic thin film transistor were specifically described. However, the organic semiconductor element of the present invention can also suitably used in a top gate-bottom contact type organic thin film transistor and a top gate-top contact type organic thin film transistor.

The organic thin film transistor described above can be suitably used for electronic paper and a display device.

(Organic Semiconductor Composition)

The first organic semiconductor composition according to the present invention is an organic semiconductor composition containing a specific compound and a solvent and preferably contains a specific compound and a solvent having boiling point of 100° C. or higher.

The second organic semiconductor composition according to the present invention is an organic semiconductor composition containing a specific polymer compound and a solvent and preferably contains a specific polymer compound and a solvent having a boiling point of 100° C. or higher.

<Solvent Having Boiling Point of 100° C. or Higher>

The first organic semiconductor composition and the second organic semiconductor composition according to the present invention preferably contains a solvent having a boiling point of 100° C. or higher.

Examples of the solvent having a boiling point of 100° C. or higher include a hydrocarbon-based solvent such as octane, decane, toluene, xylene, mesitylene, ethylbenzene, decalin, 1-methylnaphthalene, tetralin, and dimethyltetralin, a ketone-based solvent such as methyl isobutyl ketone and cyclohexanone, a halogenized hydrocarbon-based solvent such as tetrachloroethane, chlorobenzene, dichlorobenzene, chlorotoluene, 1-fluoronaphthalene, and 1-chloronaphthalene, an ester-based solvent such as butyl acetate and amyl acetate, an alcohol-based solvent such as butanol, pentanol, hexanol, cyclohexanol, methyl cellosolve, ethyl cellosolve, and ethylene glycol, an ether-based solvent such as dibutyl ether, dioxane, anisole, 4-tertiary butyl anisole, and m-dimethoxybenzene, an amide-based solvent such as N,N-dimethylformamide and N,N-dimethylacetamide, an imide-based solvent such as 1-methyl-2-pyrrolidone and 1-methyl-2-imidazolidinone, a sulfoxide-based solvent such as dimethylsulfoxide, a nitrile-based solvent such as butyronitrile and benzonitrile.

The solvent having a boiling point of 100° C. or higher may be used singly or two or more types thereof may be used in combination.

Among these, a hydrocarbon-based solvent, a halogenized hydrocarbon-based solvent, and/or an ether-based solvent is preferable, and toluene, xylene, mesitylene, tetralin, dichlorobenzene, or anisole are more preferable. If the solvent is as described above, coating properties are excellent, and thus an organic semiconductor film can be easily formed.

The organic semiconductor composition according to the present invention may contain a solvent having a boiling point of lower than 100° C., but the content thereof is preferably less than the content of the solvent having a boiling point of 100° C. or higher, and more preferably $\frac{1}{10}$ or less of the content of the solvent having a boiling point of 100° C. or higher. It is even more preferable that a solvent having a boiling point of less than 100° C. is not contained.

In order to obtain stability of an organic semiconductor composition and to form an even film, a boiling point of the solvent having a boiling point of 100° C. or higher in normal pressure is preferably 150° C. or higher, more preferably 175° C. or higher, and particularly preferably 200° C. or higher. In order to dry the specific solvent after an organic semiconductor ink is applied, the boiling point of the specific solvent is preferably 300° C. or lower, more preferably 250° C. or lower, and even more preferably 220° C. or lower.

The content of the solvent having a boiling point of 100° C. or higher in the organic semiconductor composition according to the present invention is preferably 50 to 99.9 mass %, more preferably 80 to 99.5 mass %, and even more preferably 90 to 99.0 mass % with respect to a total mass of the organic semiconductor composition.

The organic semiconductor composition according to the present invention may include other components in addition to the specific compound, the specific polymer compound, the binder polymer, and the solvent.

As the components, well-known additives may be used.

The content of the component in addition to the specific compound or the specific polymer compound, the binder polymer, and the solvent in the composition for forming the organic semiconductor according to the present invention is preferably 10 mass % or less, more preferably 5 mass % or less, even more preferably 1 mass % or less, and particularly preferably 0.1 mass % or less with respect to the total solid content. If the content is in the range described above, film formability is improved, and mobility and heat resistance of the obtained organic semiconductor are further improved. The solid content is an amount of the components excluding the volatilizable component such as the solvent.

The viscosity of the organic semiconductor composition according to the present invention is not particularly limited. However, in view of excellent coating properties, the viscosity is preferably 3 to 100 mPa·s, more preferably 5 to 50 mPa·s, and even more preferably 9 to 40 mPa·s. The viscosity according to the present invention refers to viscosity at 25° C.

As a method of measuring the viscosity, a measuring method in conformity of JIS Z8803 is preferable.

In the first organic semiconductor composition according to the present invention, it is preferable that at least a portion of the specific compound is dissolved, and it is more preferable that the entire specific compound is dissolved. However, a portion thereof may be dispersed without being dissolved.

In the second organic semiconductor composition according to the present invention, it is preferable that at least a portion of the specific polymer compound is dissolved, it is more preferable that the entire specific polymer compound is dissolved. However, a portion thereof may be dispersed without being dissolved.

The content of the specific compound in the first organic semiconductor composition according to the present invention is preferably 20 mass % or less, more preferably 0.001 to 20 mass %, even more preferably 0.001 to 15 mass %, and particularly preferably 0.01 to 10 mass % with respect to a total amount of the organic semiconductor composition. In a case where two or more types of specific compounds are used together, the total content of the specific compounds is preferably in the range described above. If the content of the specific compound is in the range described above, carrier mobility is more excellent, and preservation stability is also excellent.

The content of the specific compound is preferably 30 to 99 mass %, more preferably 50 to 95 mass %, and even more preferably 70 to 90 mass % with respect to a total solid content of the first organic semiconductor composition.

The content of the specific polymer compound in the second organic semiconductor composition according to the present invention is preferably 20 mass % or less, more preferably 0.001 to 20 mass %, even more preferably 0.001 to 15 mass %, and particularly preferably 0.01 to 10 mass % with respect to a total amount of the organic semiconductor composition. In a case where two or more types of specific polymer compounds are used together, the total content of the specific polymer compound is preferably in the range described above. If the content of the specific polymer compound is in the range described above, carrier mobility is more excellent and preservation stability is also excellent.

The content of the specific polymer compound is preferably 30 to 99 mass %, more preferably 50 to 95 mass %, and even more preferably 70 to 90 mass % with respect to a total solid content of the second organic semiconductor composition.

The method of manufacturing the first and second organic semiconductor compositions according to the present invention is not particularly limited, and well-known methods can be applied. For example, the specific compound or the specific polymer compound in a predetermined amount is added to the solvent having a boiling point of 100° C. or higher, a stirring treatment can be suitably performed, so as to obtain a desired composition. In a case where the binder polymer is used, it is suitable that the specific compound or the specific polymer compound and the binder polymer are simultaneously or sequentially added, so as to manufacture the composition.

(Organic Semiconductor Film)

The first organic semiconductor film according to the present invention contains the specific compound.

The second organic semiconductor film according to the present invention contains the specific polymer compound.

It is preferable that the first and second organic semiconductor films according to the present invention are organic semiconductor films formed respectively from the first and second organic semiconductor compositions according to the present invention.

The first and second organic semiconductor films according to the present invention each preferably contain the binder polymer.

The specific compound and the binder polymer in the first organic semiconductor film according to the present invention are the same as the specific compound and the binder polymer described above in the first organic semiconductor element according to the present invention, and preferable aspects thereof are also the same. The specific polymer compound and the binder polymer in the second organic semiconductor film according to the present invention are the same as the specific polymer compound and the binder polymer described above in the second organic semiconductor element according to the present invention, and preferable aspects thereof are also the same.

The organic semiconductor film according to the present invention may include other components in addition to the specific compound or the specific polymer compound and the binder polymer.

As the component, well-known additives may be used.

The content of the component in addition to the specific compound or the specific polymer compound and the binder polymer in the first and second organic semiconductor films according to the present invention preferably 10 mass % or less, more preferably 5 mass % or less, even more preferably 1 mass % or less, and particularly preferably 0.1 mass % or less. If the content is in the range above, film formability is improved, and mobility and heat resistance of the obtained organic semiconductor are further improved. The solid content is an amount of components other than the volatilizable components such as the solvent.

The film thickness of the organic semiconductor film according to the present invention is not particularly limited. However, in view of mobility and heat resistance of the obtained organic semiconductor, the film thickness is preferably 10 to 500 nm and more preferably 30 to 200 nm.

The organic semiconductor film according to the present invention can be suitably used in the organic semiconductor element, and can be particularly suitably used in the organic transistor (organic thin film transistor).

EXAMPLES

Hereinafter, the present invention will be more specifically described based on examples. The materials and the amount thereof used, the proportion of the materials, the content and procedure of treatments, and the like described in the following examples can be appropriately changed within a scope that does not depart from the gist of the present invention. Accordingly, the scope of the present invention is not limited to the following specific examples. Herein, unless otherwise specified, "part" and "%" are based on mass.

Compounds 1 to 9, Comparative Compounds 1 to 3, Polymer Compounds 1 to 2, and Comparative Polymer Compound 1 which were used in examples and comparative examples are provided below.

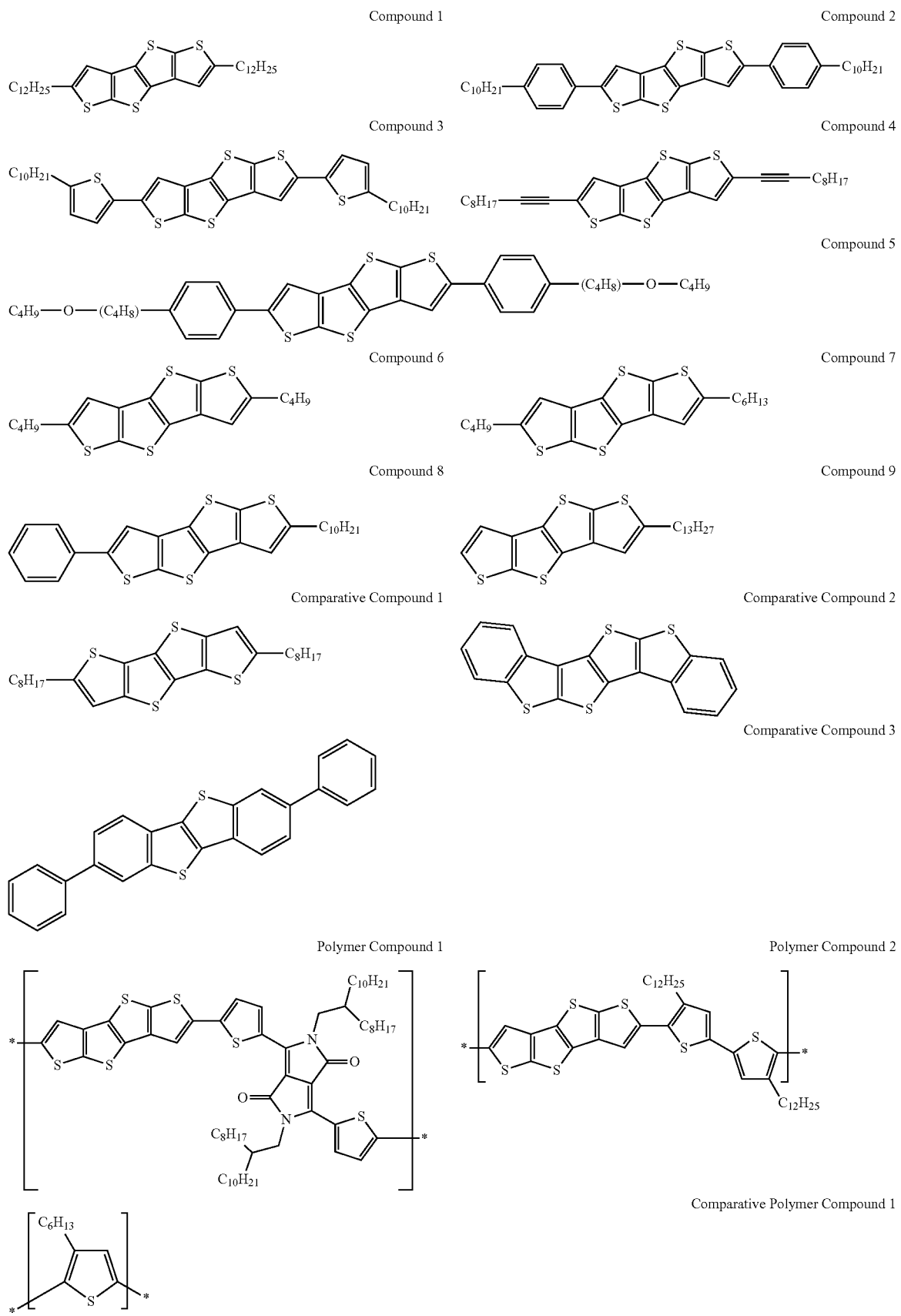

Synthesis Example

<Synthesis of Intermediate M1>
Intermediate M1 was synthesized according to Scheme 1 below.

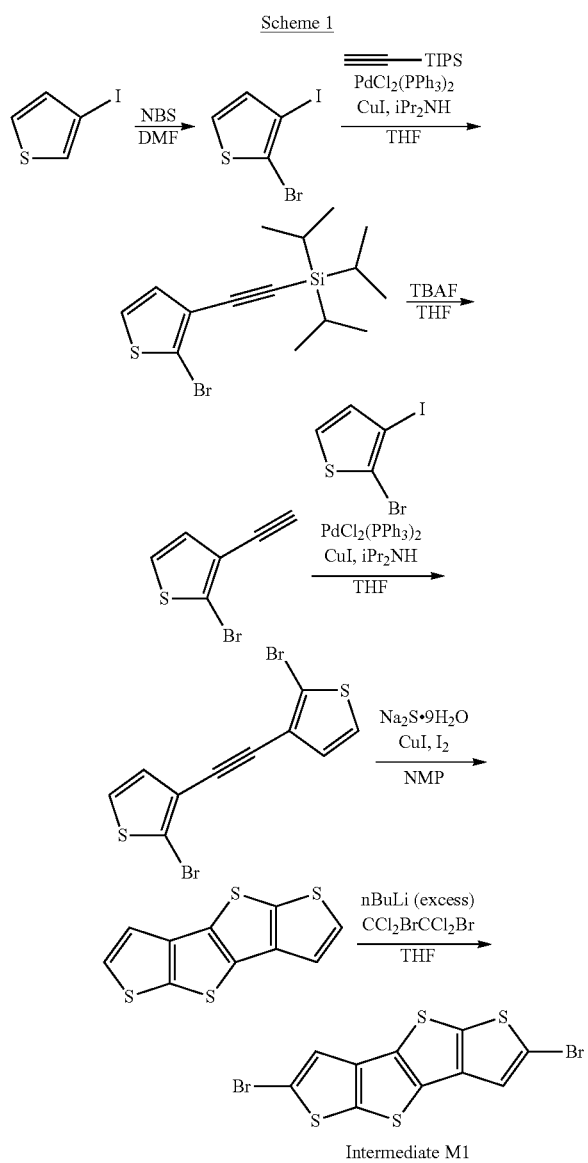

Compounds used in Scheme 1 were as below. In the description below, as the same compound, those by the same manufacturer were used.
NBS: N-Bromosuccinimide (manufactured by Wako Pure Chemical Industries, Inc.)
DMF: Dimethylformamide (manufactured by Wako Pure Chemical Industries, Inc.)
Triisopropylsilylacetylene (manufactured by Wako Pure Chemical Industries, Inc.)
$PdCl_2(PPh_3)_2$: Dichlorobis(triphenylphosphine) palladium (manufactured by Tokyo Chemical Industry Co., Ltd.)
CuI Copper iodide (manufactured by Wako Pure Chemical Industries, Inc.)
iPrNH: Diisopropylamine (manufactured by Wako Pure Chemical Industries, Inc.)
THF: Tetrahydrofuran (manufactured by Wako Pure Chemical Industries, Inc.)
TBAF: Tetra-n-butylammonium fluoride (manufactured by Wako Pure Chemical Industries, Inc.)
$Na_2S$: Sodium sulfide (manufactured by Wako Pure Chemical Industries, Inc.)
$I_2$: Iodine (manufactured by Wako Pure Chemical Industries, Inc.)
NMP: N-methyl pyrrolidone (manufactured by Kanto Chemical Co., Inc.)
nBuLi: n-Butyllithium (manufactured by Kanto Chemical Co., Inc.)
$CCl_2BrCCl_2Br$: 1,2-dibromo-1,1,2,2-tetrachloroethane (manufactured by Wako Pure Chemical Industries, Inc.)

<Synthesis of Compound 1>
Synthesis was performed by Scheme 2 below from Intermediate M1 synthesized according to Scheme 1 above and dodecyl magnesium bromide.

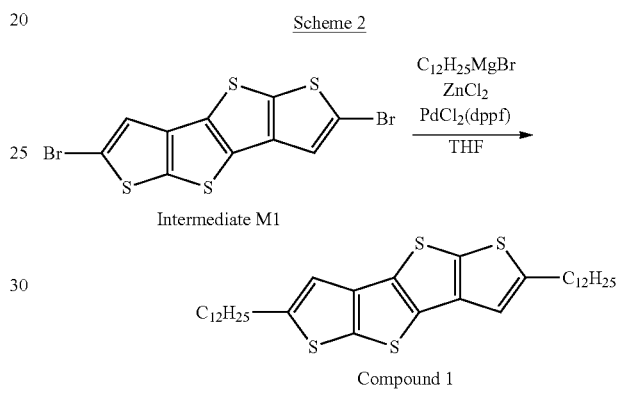

The compound used in Scheme 2 above was as below.
$C_{12}H_{25}MgBr$: Dodecyl magnesium bromide (manufactured by Sigma-Aldrich Co. LLC.)
$ZnCl_2$: Zinc chloride (manufactured by Sigma-Aldrich Co. LLC.)
$PdCl_2$(dppf): 1,1'-Bis(diphenylphosphino) ferrocene-palladium (II) dichloride-dichloromethane complex (manufactured by Wako Pure Chemical Industries, Inc.)

<Synthesis of Compound 2>
Synthesis was performed by Scheme 3 below from Intermediate MI synthesized by Scheme 1 above and p-decylphenylboronic acid.

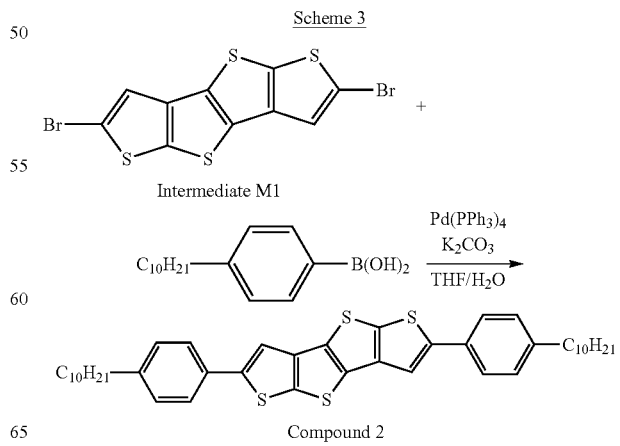

Compounds used in Scheme 3 above were as below.

p-decylphenylboron: Synthesized by the method disclosed in Tetrahedron, 2003, vol. 59, No. 24, p. 4377-4381.

Pd(PPh$_3$)$_4$: Tetrakistriphenylphosphine palladium (manufactured by Tokyo Chemical Industry Co., Ltd.)

K$_2$CO$_3$: Potassium carbonate (manufactured by Kanto Chemical Co., Inc.)

<Synthesis of Compound 3>

Synthesis was performed by Scheme 4 below from Intermediate M1 synthesized by Scheme 1 above and 2-decyl-5-trimethylstannylthiophene.

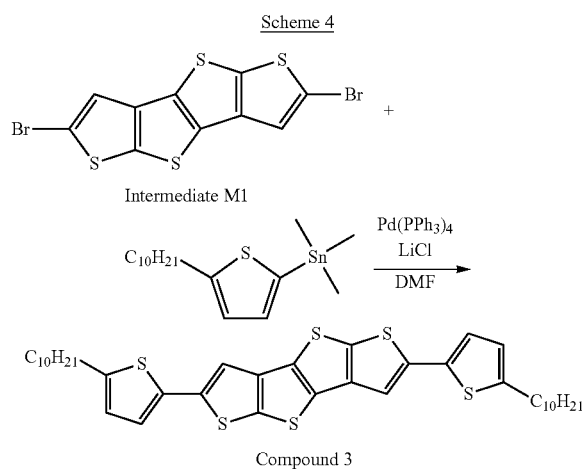

Compounds used in Scheme 4 were as below.

2-decyl-5-trimethylstannylthiophene: Synthesized by the method disclosed in US2013/168659A.

LiCl: Lithium chloride (manufactured by Sigma-Aldrich Co. LLC.)

Dimethylformamide (manufactured by Wako Pure Chemical Industries, Inc.)

<Synthesis of Compound 4>

Synthesis was performed by Scheme 5 below.

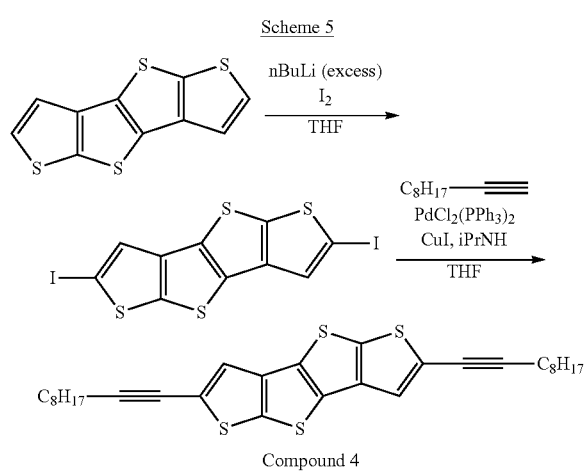

Compounds used in Scheme 5 were as below.

1-Decyne: manufactured by Tokyo Chemical Industry Co., Ltd.

<Synthesis of Compound 5>

Synthesis was performed in the same method as in the synthesis of Compound 2, except for using p-butoxybutylphenyl boronic acid instead of p-decylphenylboronic acid. p-Butoxybutylphenyl boron was synthesized by Scheme 6 below.

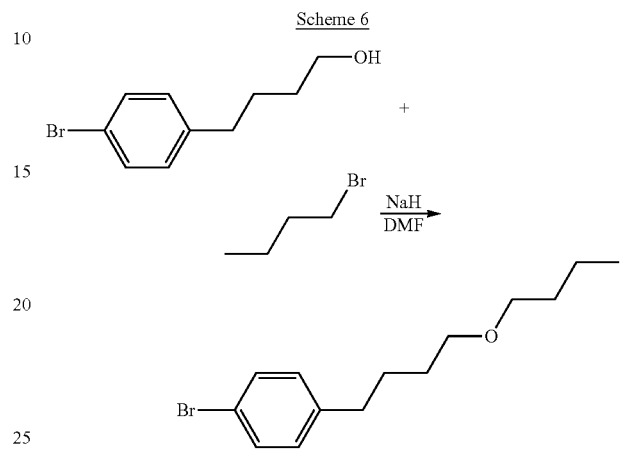

Compounds used in Scheme 6 were as below.

1-Bromobutane (manufactured by Tokyo Chemical Industry Co., Ltd.)

NaH (manufactured by Tokyo Chemical Industry Co., Ltd.)

DMF: Dimethylformamide (manufactured by Wako Pure Chemical Industries, Inc.)

4-(4-bromophenyl) butan-1-ol was synthesized by the method disclosed in Journal of Organometallic Chemistry, 2002, vol. 65, No. 1-2, p. 129-135.

<Synthesis of Compound 6>

Compound 6 was synthesized by Scheme 7 below in the same method as in Compound 1 in the synthesis of Compound 1, except for using butyl magnesium bromide instead of dodecyl magnesium bromide.

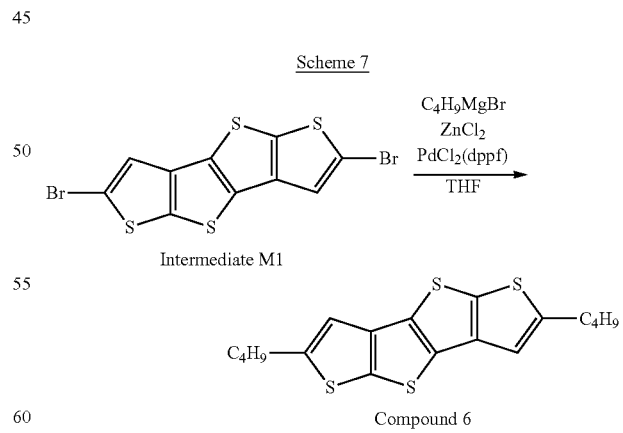

In Scheme 7, butyl magnesium bromide was prepared by causing 1-bromobutane (manufactured by Tokyo Chemical Industry Co., Ltd.) and magnesium (manufactured by Wako Pure Chemical Industries, Inc.) in tetrahydrofuran (THF, manufactured by Wako Pure Chemical Industries, Inc.).

<Synthesis of Compound 7>
Compound 7 was synthesized according to Scheme 8 below.

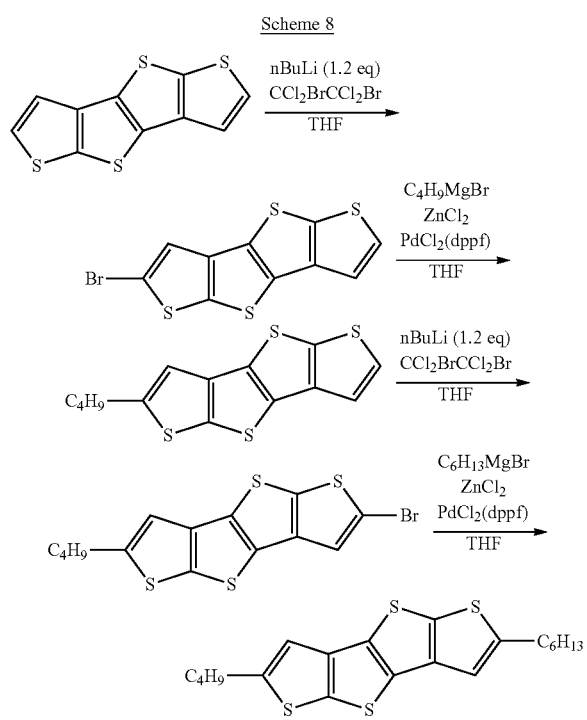

Butyl magnesium bromide used in Scheme 8 above was prepared in the same manner as in butyl magnesium bromide used in Scheme 7. Hexyl magnesium bromide was prepared in the same manner as in butyl magnesium bromide except for using 1-bromohexane (manufactured by Tokyo Chemical Industry Co., Ltd.) instead of 1-bromobutane.

<Synthesis of Compound 8>
Compound 8 was synthesized according to Scheme 9 below.

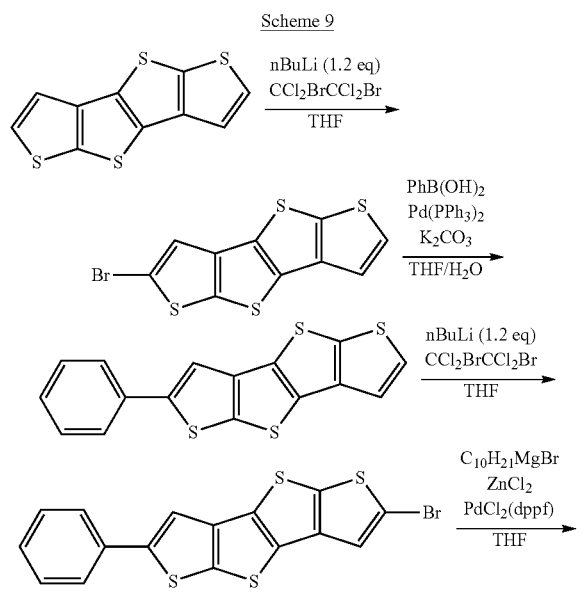

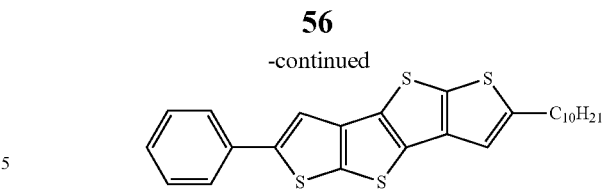

Compounds used in Scheme 9 were as below.

PhB(OH)$_2$: Phenylboronic acid (manufactured by Tokyo Chemical Industry Co., Ltd.)

C$_{10}$H$_{21}$MgBr: Prepared in the same manner as butyl magnesium bromide used in Scheme 7 above except for using 1-bromodecane (manufactured by Tokyo Chemical Industry Co., Ltd.) instead of 1-bromobutane.

<Synthesis of Compound 9>
Compound 9 was synthesized according to Scheme 10 below.

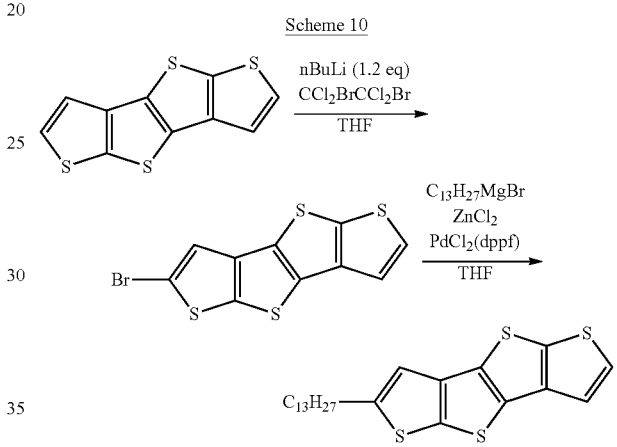

Compounds used in Scheme 10 were as below.

C$_{13}$H$_{27}$MgBr: Prepared in the same manner as in butyl magnesium bromide used in Scheme 7 above except for using 1-bromotridecane (manufactured by Tokyo Chemical Industry Co., Ltd.) instead of 1-bromobutane.

<Synthesis of Comparative Compound 1>
Comparative Compound 1 was synthesized in the method disclosed in WO2012/060460A.

<Synthesis of Comparative Compound 2>
Comparative Compound 2 was synthesized in the method disclosed in CN20120912A.

<Synthesis of Comparative Compound 3>
Comparative Compound 3 was synthesized in the method JP4581062B.

<Synthesis of Polymer Compound 1>
Polymer Compound 1 was synthesized according to Scheme 11 below.

Scheme 11

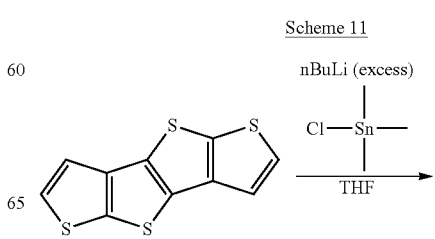

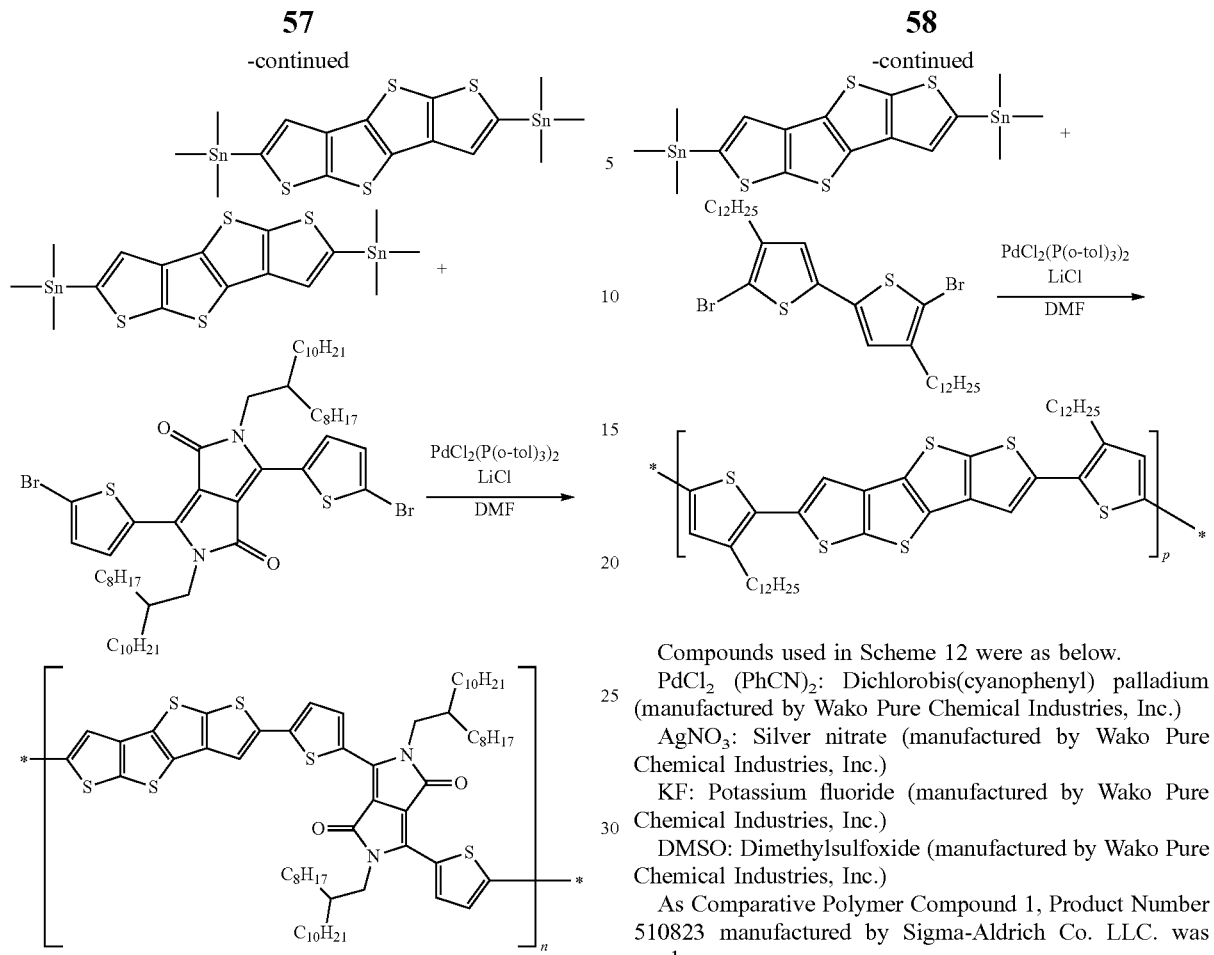

Compounds used in Scheme 12 were as below.

PdCl$_2$ (PhCN)$_2$: Dichlorobis(cyanophenyl) palladium (manufactured by Wako Pure Chemical Industries, Inc.)

AgNO$_3$: Silver nitrate (manufactured by Wako Pure Chemical Industries, Inc.)

KF: Potassium fluoride (manufactured by Wako Pure Chemical Industries, Inc.)

DMSO: Dimethylsulfoxide (manufactured by Wako Pure Chemical Industries, Inc.)

As Comparative Polymer Compound 1, Product Number 510823 manufactured by Sigma-Aldrich Co. LLC. was used.

Examples 1 to 14 and Comparative Examples 1 to 5

<Manufacturing of FET Element>

A compound, a polymer compound, a comparative compound, or a comparative polymer compound (each 1 mg) presented in Tables 1 to 3 and toluene (1 mL) were mixed and heated to 100° C., so as to obtain a non-luminescent organic semiconductor solution (organic semiconductor composition). Under the nitrogen atmosphere, this composition was casted to a substrate for measuring FET characteristics heated to 90° C. so as to form an organic semiconductor thin film (having a thickness of 200 nm), and an organic thin film transistor element for measuring FET characteristics was obtained. As the substrate for measuring FET characteristics, a silicon substrate in a bottom gate-bottom contact structure including chromium/gold (gate width W=100 mm, gate length L=100 μm) arranged in a comb-shape as source and drain electrodes and SiO$_2$ (film thickness: 200 nm) as an insulating film was used.

<Evaluation of Carrier Mobility>

With respect to the FET characteristics of the organic thin film transistor elements of the respective examples and the respective comparative examples, carrier mobility was evaluated under normal pressure and the nitrogen atmosphere by employing a semiconductor parameter analyzer (manufactured by Agilent, 4156C) to which a semi automatic prober (manufactured by Vector Semiconductor Co., Ltd., AX-2000) was connected.

Carrier mobility μ was calculated by applying a voltage of −80V between source electrodes-drain electrodes of the respective organic thin film transistor elements (FET elements), changing gate voltages in the range of +20 V to −100 V, and using an equation below indicating a drain current $I_d$.

$$I_d = (w/2L)\mu C_i (V_g - V_{th})^2$$

In the equation, L represents a gate length, W represents a gate width, $C_i$ represents capacity per unit area of an insulating layer, $V_g$ represents a gate voltage, and $V_{th}$ represents a threshold voltage.

<Solubility Evaluation>

The compounds or the comparative compounds (each 2 mass %, each 1 mass %, each 0.5 mass %, or each 0.1 mass %) according to the present invention presented in Tables 1 to 3 and toluene (1 mL) were mixed and heated to 100° C. and were left alone in room temperature for 30 minutes, so as to obtain a concentration in which precipitation was started, and solubility with respect to toluene was evaluated in four stages below. In practice, A, B, C, or D evaluation was required, A, B, or C evaluation was preferable, A or B evaluation was more preferable, and A evaluation was even more preferable.

—Evaluation Standard—
A: No precipitation in 2 mass %
B: No precipitation in 1 mass % and precipitation in 2 mass %
C: No precipitation in 0.5 mass % and precipitation in 1 mass %
D: No precipitation in 0.1 mass % and precipitation in 0.5 mass %
E: Precipitation in 0.1 mass %

<Coating Film Formability Evaluation>

The compounds or the comparative compounds (each 1 mg) presented in Tables 1 to 3 and toluene (1 mL) were mixed and heated to 100° C., so as to obtain a nonluminescent organic semiconductor solution (organic semiconductor composition). Under the nitrogen atmosphere, this composition was casted to an entire surface of a substrate on which channels for 50 elements were formed and which was heated to 90° C. so as to form an organic semiconductor thin film, and 50 elements of organic thin film transistor elements for measuring FET characteristics was obtained.

—Evaluation Standard—
Coating film formability A: 45 or more (90% or greater) elements were driven as TFT elements among the obtained 50 elements.
Coating film formability B: Less than 45 (less than 90%) elements were driven as TFT elements among the obtained 50 elements.

<Heat Resistance Evaluation>

After the manufactured respective organic thin film transistor elements were heated for one hour at 130° C. in a nitrogen glove box, carrier mobility µ was measured, so as to calculate a carrier mobility maintenance rate after heating by the equation below.

Carrier mobility maintenance rate after heating (%)=Mobility (after heating)/Mobility (initial value)

Obtained results were evaluated according to evaluation standards below.

—Evaluation Standard—
A: 90% or greater.
B: 70% or greater and less than 90%.
C: 40% or greater and less than 70%.
D: 20% or greater and less than 40%.
E: Less than 20%.

In Tables 1 and 2, N/A represents that evaluation was not performed since TFT characteristics were not exhibited, and mobility was not able to be measured.

Examples 15 to 17 and Comparative Example 6: Ink Jet Coating

The organic semiconductor composition manufactured for the coating film formability evaluation was applied to a substrate for measuring FET characteristics by an ink jet printing. Specifically, DPP2831 (manufactured by FUJIFILM Global Graphic Systems Co., Ltd.) was used as an inkjet device and 10 pL heads were used, so as to form a solid film with a jetting frequency of 2 Hz and a pitch between dots of 20 µm. Thereafter, drying was performed for one hour at 70° C., so as to form an organic semiconductor film, and the organic TFT element for measuring FET characteristics was obtained.

In the examples and the comparative examples, carrier mobility and heat resistance with respect to the organic TFT element that were able to be obtained by ink jet printing were evaluated.

<Atmospheric Stability Evaluation>

Atmospheric stability was evaluated by changes of threshold values after repetitive driving.

A voltage of −80 V was applied between source electrodes and drain electrodes of the respective organic thin film transistor elements (FET elements), measurement as in (a) was performed 100 times with a gate voltage in the range of 20 V to −100 V, a difference ($|V_{after} - V_{before}|$) between a threshold value $V_{before}$ before the repetitive driving and a threshold value $V_{after}$ after the repetitive driving was evaluated in three stages below. As this value is smaller, repetitive driving stability of the element is higher and preferable.

—Evaluation Standard—
A: $|V_{after} - V_{before}| \leq 1$ V
B: $1$ V $< |V_{after} - V_{before}| \leq 5$ V
C: $5$ V $< |V_{after} - V_{before}| \leq 10$ V
D: $10$ V $< |V_{after} - V_{before}| \leq 15$ V
E: $|V_{after} - V_{before}| > 15$ V

TABLE 1

|  | Organic semiconductor compound | Mobility (Coating) | Solubility | Coating film formability | Heat resistance |
|---|---|---|---|---|---|
| Example 1 | Compound 1 | 0.8 | A | A | A |
| Example 2 | Compound 2 | 0.7 | B | A | A |
| Example 3 | Compound 3 | 0.6 | B | A | A |
| Example 4 | Compound 4 | 0.3 | A | A | A |
| Example 5 | Compound 5 | 0.2 | A | A | A |
| Example 6 | Compound 6 | 0.1 | A | A | A |
| Example 7 | Compound 7 | 0.09 | A | A | B |
| Example 8 | Compound 8 | 0.05 | B | A | B |

TABLE 1-continued

| | Organic semiconductor compound | Mobility (Coating) | Solubility | Coating film formability | Heat resistance |
|---|---|---|---|---|---|
| Example 9 | Compound 9 | 0.03 | B | A | C |
| Comparative Example 1 | Comparative Compound 1 | $8 \times 10^{-3}$ | C | B | D |
| Comparative Example 2 | Comparative Compound 2 | No characteristics | D | B | N/A |
| Comparative Example 3 | Comparative Compound 3 | No characteristics | D | B | N/A |

TABLE 2

| | Organic semiconductor compound | Polymer | Mobility (Coating) | Solubility | Coating film formability | Heat resistance |
|---|---|---|---|---|---|---|
| Example 10 | Compound 1 | PαMS | 1 | A | A | A |
| Example 11 | Compound 2 | PαMS | 0.8 | B | A | A |
| Example 12 | Compound 6 | PαMS | 0.5 | A | A | A |
| Example 13 | Compound 8 | PαMS | 0.1 | B | A | A |
| Example 14 | Compound 9 | PαMS | 0.06 | B | A | B |
| Comparative Example 4 | Comparative Compound 1 | PαMS | 0.01 | C | A | D |
| Comparative Example 5 | Comparative Compound 2 | PαMS | No characteristics | D | B | N/A |

TABLE 3

| | Organic semiconductor compound | Number-average molecular weight | Mobility (Coating) | Solubility | Coating film formability | Heat resistance | Atmospheric stability (Threshold shift) |
|---|---|---|---|---|---|---|---|
| Example 15 | Polymer Compound 1 | 120,000 | 0.3 | A | A | A | A |
| Example 16 | Polymer Compound 1 | 160,000 | 0.3 | A | A | A | A |
| Example 17 | Polymer Compound 2 | 100,000 | 0.2 | A | A | A | A |
| Comparative Example 6 | Comparative Polymer Compound 1 | Unclear since this was a purchased product | $3 \times 10^{-3}$ | A | A | D | D |

EXPLANATION OF REFERENCES

10: substrate
20: gate electrode
30: gate insulating film
40: source electrode
42: drain electrode
50: organic semiconductor film
60: sealing layer
100,200: organic thin film transistor

What is claimed is:
1. A compound represented by Formula 1, or an oligomer or a polymer, the oligomer or the polymer comprising a constitutional repeating unit including a structure represented by Formula 3:

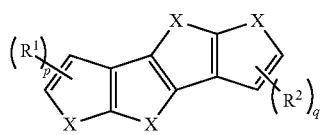

(1)

wherein, in Formula 1, X represents a chalcogen atom, p and q each independently represent an integer of 0 to 2, and $R^1$ and $R^2$ each independently represent a halogen atom or a group represented by Formula W below,

—S-L-T        (W)

wherein, in Formula W, S represents a single bond or —$(C(R^s)_2)_n$—, each $R^s$ independently represents a hydrogen atom or a halogen atom, n represents an integer of 1 to 17, L represents a single bond, a divalent linking group represented by any one of Formulae L-1 to L-15 below, or a divalent linking group obtained by bonding two or more divalent linking groups represented by any one of Formulae L-1 to L-15 below, and T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is 2 or greater, a siloxane group, an oligosiloxane group having two or more silicon atoms, or a trialkylsilyl group, and

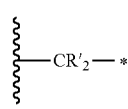

(L-1)

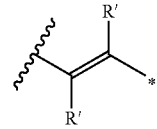

(L-2)

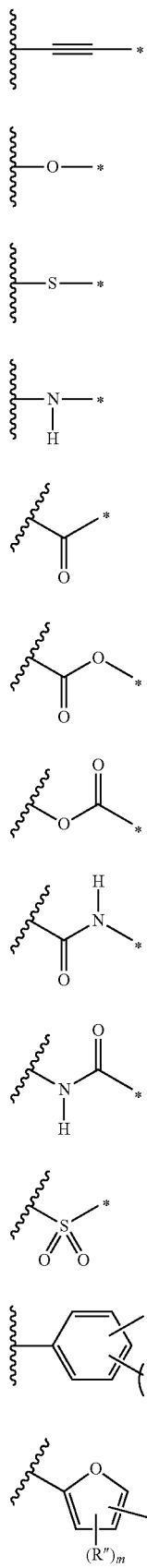
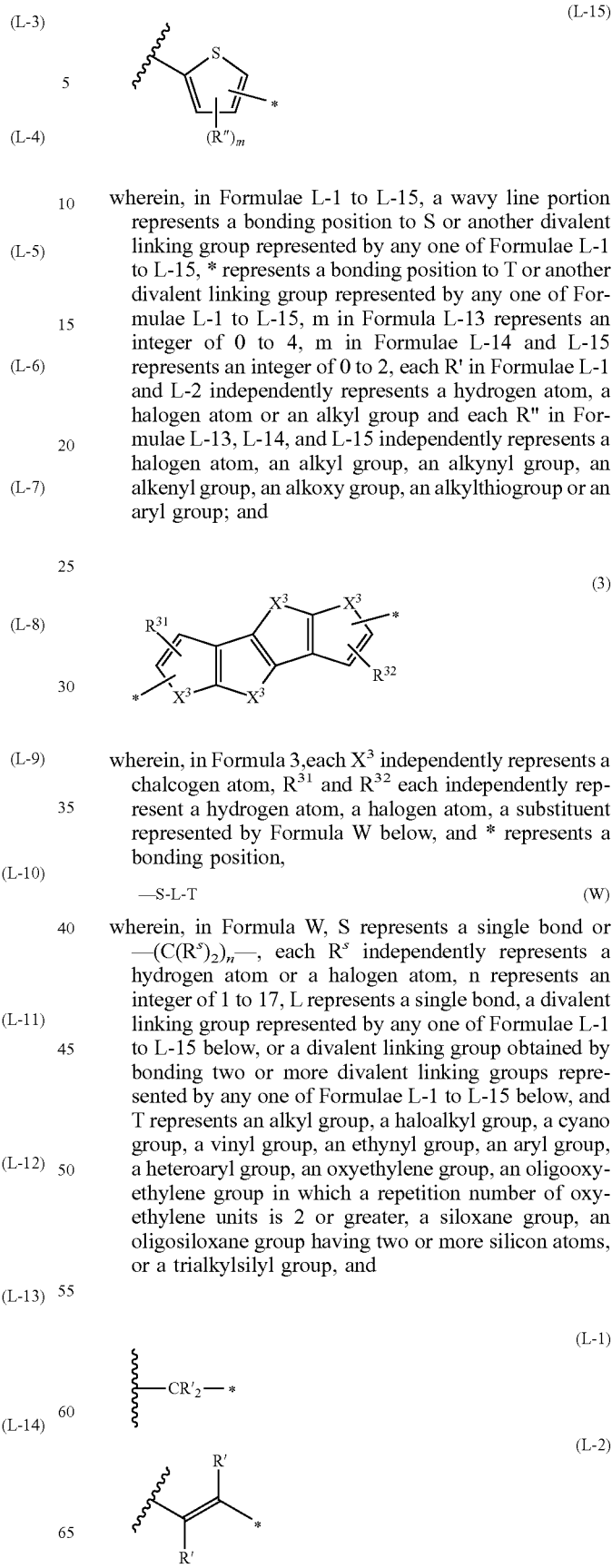

wherein, in Formulae L-1 to L-15, a wavy line portion represents a bonding position to S or another divalent linking group represented by any one of Formulae L-1 to L-15, * represents a bonding position to T or another divalent linking group represented by any one of Formulae L-1 to L-15, m in Formula L-13 represents an integer of 0 to 4, m in Formulae L-14 and L-15 represents an integer of 0 to 2, each R' in Formulae L-1 and L-2 independently represents a hydrogen atom, a halogen atom or an alkyl group and each R" in Formulae L-13, L-14, and L-15 independently represents a halogen atom, an alkyl group, an alkynyl group, an alkenyl group, an alkoxy group, an alkylthiogroup or an aryl group; and wherein, in Formula 3, each $X^3$ independently represents a chalcogen atom, $R^{31}$ and $R^{32}$ each independently represent a hydrogen atom, a halogen atom, a substituent represented by Formula W below, and * represents a bonding position, $$—S-L-T \qquad (W)$$

wherein, in Formula W, S represents a single bond or $—(C(R^s)_2)_n—$, each $R^s$ independently represents a hydrogen atom or a halogen atom, n represents an integer of 1 to 17, L represents a single bond, a divalent linking group represented by any one of Formulae L-1 to L-15 below, or a divalent linking group obtained by bonding two or more divalent linking groups represented by any one of Formulae L-1 to L-15 below, and T represents an alkyl group, a haloalkyl group, a cyano group, a vinyl group, an ethynyl group, an aryl group, a heteroaryl group, an oxyethylene group, an oligooxyethylene group in which a repetition number of oxyethylene units is 2 or greater, a siloxane group, an oligosiloxane group having two or more silicon atoms, or a trialkylsilyl group, and

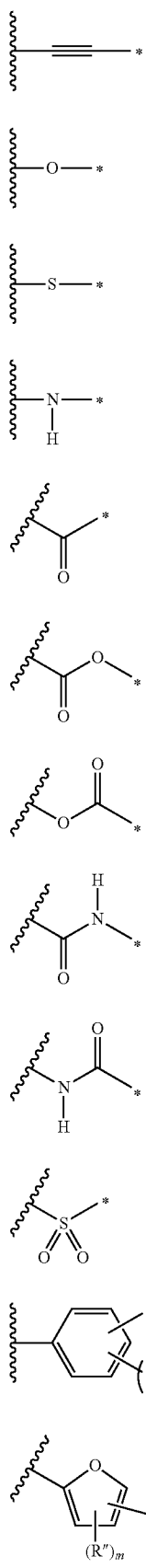

(L-3)

(L-4)

(L-5)

(L-6)

(L-7)

(L-8)

(L-9)

(L-10)

(L-11)

(L-12)

(L-13)

(L-14)

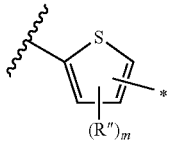

(L-15)

wherein, in Formulae L-1 to L-15, a wavy line portion represents a bonding position to S or another divalent linking group represented by any one of Formulae L-1 to L-15, * represents a bonding position to T or another divalent linking group represented by any one of Formulae L-1 to L-15, m in Formula L-13 represents an integer of 0 to 4, m in Formulae L-14 and L-15 represents an integer of 0 to 2, each R' in Formulae L-1 and L-2 independently represents a hydrogen atom, a halogen atom or an alkyl group, and each R" in Formulae L-13, L-14, and L-15 independently represents a halogen atom, an alkyl group, an alkynyl group, an alkenyl group, an alkoxy group, an alkylthiogroup or an aryl group.

2. An organic semiconductor element comprising any one selected from the group consisting of the compound, oligomer and polymer according to claim 1 in a semiconductor active layer.

3. The organic semiconductor element according to claim 2,
   wherein at least one of p or q in Formula 1 represents 1 or 2.

4. The organic semiconductor element according to claim 2,
   wherein at least one of p or q in Formula 1 represents 1 or 2, and
   wherein at least one of $R^1$ or $R^2$ represents a group represented by Formula W.

5. The organic semiconductor element according to claim 2,
   wherein p and q in Formula 1 represent 1.

6. The organic semiconductor element according to claim 2,
   wherein the compound represented by Formula 1 is a compound represented by Formula 2-1 or 2-2 below,

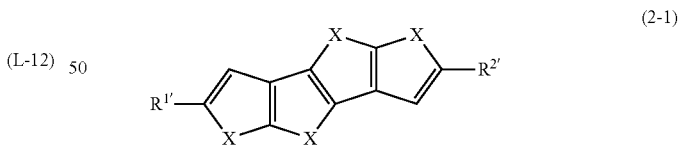

(2-1)

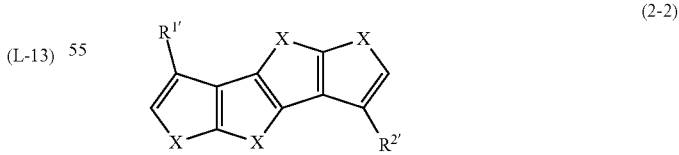

(2-2)

wherein each X in Formula 2-1 and 2-2 independently represents a chalcogen atom, and $R^{1'}$ and $R^{2'}$ each independently represent a group represented by Formula W.

7. The organic semiconductor element according to claim 2,
   wherein every X is an S atom.

8. The organic semiconductor element according to claim 2,
wherein a compound represented by Formula 1 is point symmetric about a point A below,

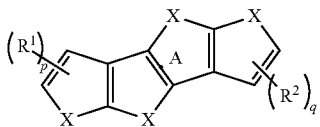

(1)

wherein, in the compound represented by Formula 1 that is point symmetric about point A, p and q each represent an integer of 0 to 2, and $R^1$ and $R^2$ each represent a halogen atom or a group represented by Formula W.

9. The organic semiconductor element according to claim 2,
wherein a sum of the numbers of carbon atoms of a group represented by Formula W is from 2 to 40.

10. The organic semiconductor element according to claim 2,
wherein L in Formula W represents a divalent linking group represented by any one selected from the group consisting of Formulae L-1 to L-4 and L-13 to L-15, or by a divalent linking group obtained by bonding two or more divalent linking groups represented by any one selected from the group consisting of Formulae L-1 to L-4 and L-13 to L-15.

11. The organic semiconductor element according to claim 2,
wherein an oligomer or a polymer having a constitutional repeating unit including a structure represented by Formula 3 is conjugated in a main chain direction.

12. The organic semiconductor element according to claim 2,
wherein a constitutional repeating unit including a structure represented by Formula 3 further includes a structure represented by Formula Z below, —Ar$^1$—(V)$_{p\text{-}Ar}$$^2$— (Z)

wherein, in Formula Z, Ar$^1$ and Ar$^2$ each independently represent a single bond, a vinylene group, an ethynylene group, an arylene group, a heteroarylene group, or a divalent group obtained by bonding two or more of these, and
wherein V represents a single bond or a divalent conjugate group having from 2 to 40 carbon atoms, p represents 1 to 6, two or more instances of V may be identical to or different from each other when p is 2 or greater, and all of Ar$^1$, Ar$^2$, and V are not simultaneously single bonds.

13. The organic semiconductor element according to claim 12
wherein the oligomer or the polymer having a constitutional repeating unit including a structure represented by Formula 3 is an oligomer or a polymer obtained by linking a structure represented by Formula 3 and a structure represented by Formula Z with each other.

14. The organic semiconductor element according to claim 12,
wherein V in Formula Z represents a divalent linking group represented by any one selected from the group consisting of Formulae V$_D$-1 to V$_D$-16, and V$_A$-1 to V$_A$-11 below, and

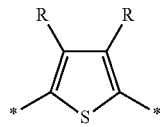 (V$_D$-1)

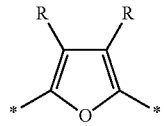 (V$_D$-2)

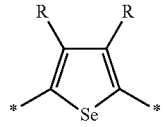 (V$_D$-3)

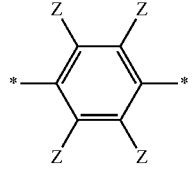 (V$_D$-4)

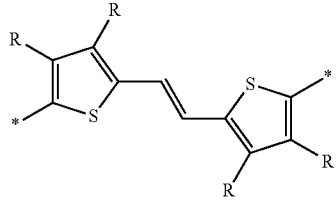 (V$_D$-5)

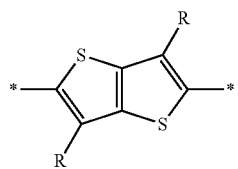 (V$_D$-6)

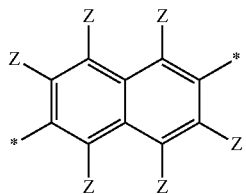 (V$_D$-7)

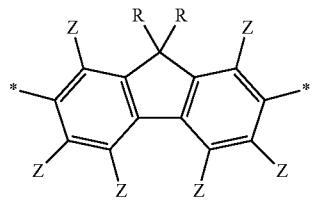 (V$_D$-8)

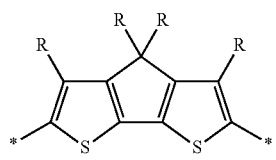 (V$_D$-9)

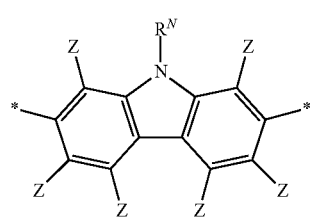 (V_D-10)
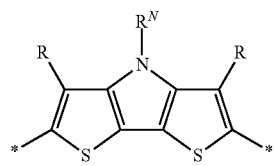 (V_D-11)
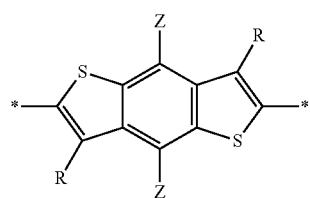 (V_D-12)
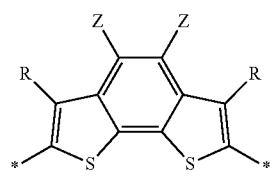 (V_D-13)
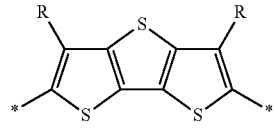 (V_D-14)
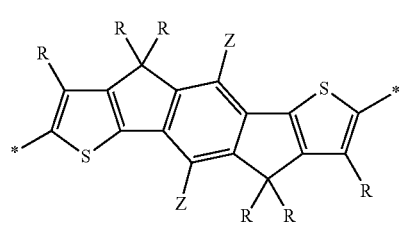 (V_D-15)
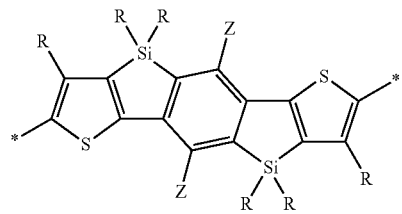 (V_D-16)
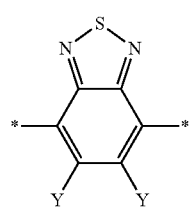 (V_A-1)
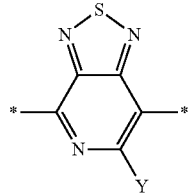 (V_A-2)
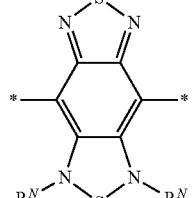 (V_A-3)
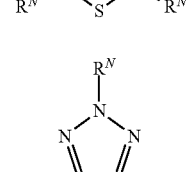 (V_A-4)
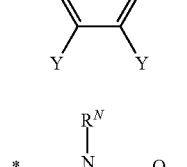 (V_A-5)
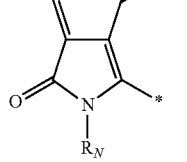 (V_A-6)
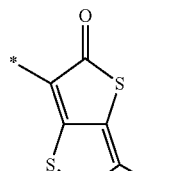 
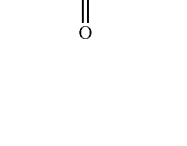 (V_A-7)
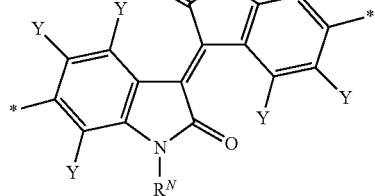

-continued

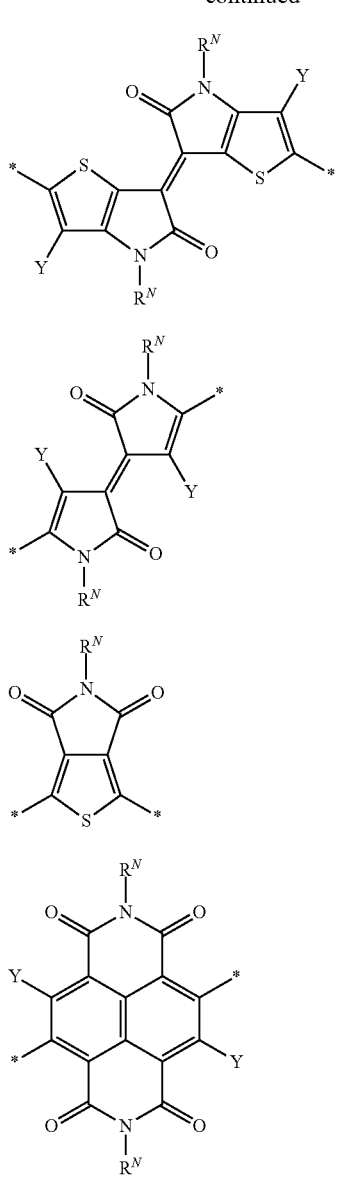

(V$_A$-8)

(V$_A$-9)

(V$_A$-10)

(V$_A$-11)

wherein each R in Formulae V$_D$-1 to V$_D$-3, V$_D$-5, V$_D$-6, V$_D$-8, V$_D$-9, and V$_D$-11 to V$_D$-16 independently represents a hydrogen atom, a halogen atom, or an alkyl group, instances of R that are adjacent to each other may be bonded to each other to form a ring, each Z in Formulae V$_D$-4, V$_D$-7, V$_D$-8, V$_D$-10, V$_D$-12, V$_D$-13, V$_D$-15, and V$_D$-16 independently represents a hydrogen atom, a halogen atom, an alkyl group, or an alkoxy group, instances of Z that are adjacent to each other may be bonded to each other to form a ring, each R$^N$ in Formulae V$_D$-10, V$_D$-11, V$_A$-4, V$_A$-5, and V$_A$-7 to V$_A$-11 independently represents an alkyl group, instances of R$^N$ that are adjacent to each other may be bonded to each other to form a ring, each Y in Formulae V$_A$-1, V$_A$-2, V$_A$-3, V$_A$-4, V$_A$-7 to V$_A$-9, and V$_A$-11 independently represents a hydrogen atom, an alkyl group, an alkoxy group, CN, or a halogen atom, instances of Y that are adjacent to each other may be bonded to each other to form a ring, and * represents a bonding position.

15. The organic semiconductor element according to claim 12, wherein p in Formula Z represents 1.

16. The organic semiconductor element according to claim 12,
wherein Ar$^1$ and Ar$^2$ in Formula Z each independently represent a single bond or a divalent linking group represented by Formula Ar-1 or Ar-2 below,

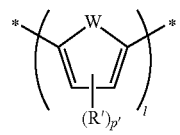

(Ar-1)

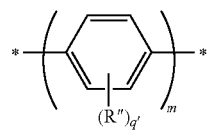

(Ar-2)

wherein, in Formula Ar-1, each R' independently represents an alkyl group, p' represents an integer of 0 to 2, instances of R' that are adjacent to each other may form a ring, W represents a chalcogen atom, and l represents an integer of 1 to 4, and
wherein each R" in Formula Ar-2 independently represents an alkyl group or an alkoxy group, q' represents an integer of 0 to 4, instances of R" that are adjacent to each other may form a ring, m represents an integer of 1 to 4, and * represents a bonding position.

17. An organic semiconductor composition comprising:
any one selected from the group consisting of the compound, the oligomer and the polymer according to claim 1; and
a solvent.

18. The organic semiconductor composition according to claim 17, further comprising:
a binder polymer.

19. A method of manufacturing an organic semiconductor element, comprising:
an applying step of applying the organic semiconductor composition according to claim 17 to a substrate by an ink jet method or a flexographic printing method; and
a removing step of removing at least a portion of the solvent from the applied organic semiconductor composition.

20. An organic semiconductor film formed from forming the organic semiconductor composition according to claim 17.

* * * * *